US008288090B2

(12) United States Patent
Fomsgaard

(10) Patent No.: US 8,288,090 B2
(45) Date of Patent: Oct. 16, 2012

(54) INFLUENZA VACCINES

(75) Inventor: Anders Fomsgaard, Frederiksberg (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

(21) Appl. No.: 12/689,547

(22) Filed: Jan. 19, 2010

(65) Prior Publication Data

US 2010/0160421 A1 Jun. 24, 2010

Related U.S. Application Data

(62) Division of application No. 12/156,456, filed on May 30, 2008, now abandoned.

(60) Provisional application No. 60/934,117, filed on Jun. 11, 2007.

(30) Foreign Application Priority Data

May 31, 2007 (DK) ................................ 2007 00784
Jun. 11, 2007 (DK) ................................ 2007 00834

(51) Int. Cl.
*C12Q 1/70* (2006.01)

(52) U.S. Cl. .... 435/5; 424/202.1; 424/204.1; 424/209.1

(58) Field of Classification Search ........................ None
See application file for complete search history.

(56) References Cited

U.S. PATENT DOCUMENTS

| | | | | |
|---|---|---|---|---|
| 6,649,170 | B1 | 11/2003 | Lindblad et al. | |
| 7,749,520 | B2 | 7/2010 | Davidsen et al. | |
| 2002/0165176 | A1* | 11/2002 | Haynes et al. | 514/44 |
| 2004/0057963 | A1 | 3/2004 | Andersen et al. | |
| 2004/0087521 | A1* | 5/2004 | Donnelly et al. | 514/44 |
| 2005/0191308 | A1 | 9/2005 | Lindblad et al. | |
| 2008/0008724 | A1 | 1/2008 | Aagaard et al. | |
| 2010/0015171 | A1 | 1/2010 | Dietrich et al. | |

FOREIGN PATENT DOCUMENTS

WO WO 2006/063101 A2 6/2006

OTHER PUBLICATIONS

Lambert and Fauci, Review Article Current Concepts Influenza Vaccines for the Future, 2010, New England Journal of Medicine, vol. 363, pp. 2036-2044.*
Ko et al., Optimization of Codon Usage Enhances the Immunogenicity of a DNA Vaccine Encoding Mycobacterial Antigen Ag85B, 2005, Infection and Immunity, vol. 73, No. 9, pp. 5666-5674.*
GenBank Accession AY130766, Influenza A virus (A/Brevig_Mission/1/1918(H1N1)) matrix protein 1 and matrix protein 2 genes, complete cds., 2002.*
GenBank Accession AY744935, Influenza A virus (A/Brevig Mission/1/1918(H1N1)) nucleoprotein (np) mRNA, complete cds., 2004.*
Antonovics, J. et al, Molecular Virology: Was the 1918 Flu Avian in Origin? Nature, vol. 440(7088):E9; Discussion, (Apr. 27, 2006).
Bragstad et al, New Avian Influenza A Virus Subtype Combination H5N7 Identified in Danish Mallard Ducks, Virus Research, 109, pp. 181-190, (May 2005).
Caton et al, The Antigenic Structure of the Influenza Virus A/PR/8/34 Hemagglutinin (H1 Subtype), Cell, vol. 31, pp. 417-427, (Dec. 1982).
Chen et al, Cross-Protection Against a Lethal Influenza Virus Infection by DNA Vaccine to Neuraminidase, Vaccine, 18, pp. 3214-3222, (Aug. 2000).
Corbet et al, Construction, Biological Activity, and Immunogenicity of Synthetic Envelope DNA Vaccines Based on a Primary, CCR5-Tropic, Early HIV type 1 Isolate (BX08) with Human Codons, Aids Research and Human Retroviruses, vol. 16, No. 18, pp. 1997-2008, (Dec. 2000).
Davis et al, Plasmid DNA is Superior to Viral Vectors for direct Gene Transfer into Adult Mouse Skeletal Muscle, Human Gene Therapy, 4:733-740, (Dec. 1993).
Donnelly et al, Preclinical Efficacy of a Prototype DNA Vaccine: Enhanced Protection Against Antigenic Drift in Influenza Virus, Nat Med, 1(6):583-7, (Jun. 1995).
Epstein et al, Protection Against Multiple Influenza A Subtypes by Vaccination with Highly Conserved Nucleoprotein, Vaccine 23, pp. 5404-5410, (Nov. 2005).
Gibbs, MJ, Molecular Virology: Was the 1918 Pandemic Caused by a Bird Flu? Nature, vol. 440(7088):E8; Discussion, (Apr. 27, 2006).
Hall, Thomas, BioEdit: A User-Friendly Biological Sequence Alignment Editor and Analysis Program for Windows 95/98/NT, Nucleic Acids Symposium Series No. 41, pp. 95-98, (1999).
Johnson et al, Updating the Accounts: Global Mortality of the 1918-1920 "Spanish" Influenza Pandemic, Bull. Hist. Med., 76:105-115, (Spring 2002).
Kawaoka et al, Avian-to-Human Transmission of the PB1 Gene of Influenza A Viruses in the 1957 and 1968 Pandemics, Journal of Virology, vol. 63, No. 11, pp. 4603-4608, (Nov. 1989).
Kobasa et al, Enhanced Virulence of Influenza A Viruses with the Haemaglutinin of the 1918 Pandemic Virus, Nature, vol. 431, pp. 703-707, (Oct. 7, 2004).
Kodihalli et al, Cross-Protection Among Lethal H5N2 Influenza Viruses Induced by DNA Vaccine to the Hemagglutinin, Journal of Virology, vol. 71, No. 5, pp. 3391-3396, (May 1997).

(Continued)

*Primary Examiner* — Benjamin P Blumel
(74) *Attorney, Agent, or Firm* — Howson & Howson LLP

(57) ABSTRACT

Described herein are vaccines and the use of naked DNA and/or RNA encoding hemagglutinin (HA) from pandemic influenza, e.g., the 1918 H1N1 and/or the 1957 H2N2 and/or the 1968 H3N2 influenza A virus, as a vaccine component against present day and coming H1, H2, H3, H5, N1, N2 containing influenza A infections in humans and swine optionally with the naked DNA and/or RNA encoding Neuraminidase (NA) and/or matrix protein (M) and/or the nucleoprotein (NP) from pandemic influenza virus included. If the vaccine components are used as DNA or RNA vaccines with or without the corresponding protein, the codons can optionally be "humanized" using preferred codons from highly expressed mammalian genes and the administration of this DNA vaccine can be by saline or buffered saline injection of naked DNA or RNA, or injection of DNA plasmid or linear gene expressing DNA fragments coupled to particles. Addition of the matrix protein (M) and/or the nucleoprotein (NP) from the 1918 influenza strain is also disclosed.

14 Claims, 3 Drawing Sheets

OTHER PUBLICATIONS

Kodihalli et al, DNA Vaccine Encoding Hemagglutinin Provides Protective Immunity Against H5N1 Influenza Virus Infection in Mice, Journal of Virology, vol. 73, No. 3, pp. 2094-2098, (Mar. 1999).
Kodihalli et al, Strategies for Inducing Protection Against Avian Influenza A Virus Subtypes with DNA Vaccines, Vaccine 18, pp. 2592-2599, (May 2000).
Kong et al, Protective Immunity to Lethal Challenge of the 1918 Pandemic Influenza Virus by Vaccination, PNAS, vol. 103, No. 43, pp. 15987-15991, (Oct. 24, 2006).
Lindstrom et al, Genetic Analysis of Human H2N2 and Early H3N2 Influenza Viruses, 1957-1972: Evidence for Genetic Divergence and Multiple Reassortment Events, Virology, 328, pp. 101-119, (Oct. 2004).
Liu et al., DNA Vaccines: Recent Developments and Future Possibilities, Human Gene Therapy, Nov. 2006, pp. 1051-1061, vol. 17.
Ljungberg et al, DNA Vaccination of Ferrets with Chimeric Influenza A Virus Hemaglutinin (H3) Genes, Vaccine, 20, pp. 2045-2052, (May 2002).
Reid et al, Origin and Evolution of the 1918 "Spanish" Influenza Virus Hemagglutinin Gene, Proc. Natl. Acad. Sci. vol. 96, pp. 1651-1656, (Feb. 1999).
Reid et al, Characterization of the 1918 "Spanish" Influenza Virus Neuraminidase Gene, PNAS, vol. 97, No. 12, pp. 6785-6790, (Jun. 6, 2000).
Seo et al, Lethal H5N1 Influenza Viruses Escape Host Anti-Viral Cytokine Responses, Nature Medicine, vol. 8, No. 9, (Sep. 2002).
Smith et al, Lessons for Human Influenza from Pathogenicity Studies with Ferrets, Reviews of Infectious Diseases, vol. 10, No. 1, (Jan.-Feb. 1988).
Spackman et al, Development of a Real-Time Reverse Transcriptase PCR Assay for Type A Influenza Virus and the Avian H5 and H7 Hemagglutinin Subtypes, Journal of Clinical Microbiology, vol. 40, No. 9, (Sep. 2002).
Tamura et al, Mechanisms of Broad Cross-Protection Provided by Influenza Virus Infection and Their Application to Vaccines, J. Infect. Dis., 58, pp. 195-207, (Aug. 2005).
Talon et al, Activation of Interferon Regulatory Factor 3 is Inhibited by the Influenza A Virus NS1 Protein, Journal of Virology, vol. 74, No. 17, pp. 7989-7996, (Sep. 2000).
Taubenberger et al, Characterization of the 1918 Influenza Virus Polymerase Genes, Nature, vol. 437, pp. 889-893, (Oct. 6, 2005).
Tumpey et al, Characterization of the Reconstructed 1918 Spanish Influenza Pandemic Virus, Science, vol. 310, (Oct. 7, 2005).
Tumpey et al, Pathogenicity and Immunogenicity of Influenza Viruses with Genes from the 1918 Pandemic Virus, PNAS, vol. 101, No. 9, (Mar. 2, 2004).
Tumpey et al, Pathogenicity of Influenza Viruses with Genes form the 1918 Pandemic Virus: Functional Roes of alveolar Macrophages and Neutrophils in Limiting Virus Replication and Mortality in Mice, Journal of Virology, pp. 14933-14944, vol. 79, No. 23, (Dec. 2005).
Ulmer et al, Protective $CD4^+$ and $CD8^+$ T Cells against Influenza Virus Induced by Vaccination with Nucleoprotein DNA, Journal of Virology, vol. 72, No. 7, pp. 5648-5653, (Jul. 1998).
Wang et al, Influenza A Virus NS1 Protein Prevents Activation of NF-κB and Induction of Alpha/Beta Interferon, Journal of Virology, vol. 74, No. 24, pp. 11566-11573, (Dec. 2000).
Wang et al, Intranasal Immunization with Liposome-Encapsulated Plasmid DNA Encoding Influenza Virus Hemagglutinin Elicits Mucosal, Cellular and Humoral Immune Responses, Journal of Clinical Virology, 31 Suppl 1:S99-106 (Dec. 2004).
Wang et al, Hemagglutinin (HA) Proteins from H1 and H3 Serotypes of Influenza A Viruses Require Different Antigen Designs for the Induction of Optimal Protective Antibody Responses as Studied by Codon-Optimized HA DNA Vaccines, Journal of Virology, vol. 80, No. 23, pp. 11628-11637, (Dec. 2006).
Webster et al, Protection of Ferrets against Influenza Challenge with a DNA Vaccine to the Haemagglutinin, Vaccine, 12(16):1495-1498, (Dec. 1994).
Xie, et al, Evaluating the vaccine potential of an influenza A viral hemagglutinin and matrix double insertion DNA plasmid, Vaccine, 2007, pp. 7649-7655.
Genbank Accession # CY008158, Influenza A virus (A/Beijing/1/68(HSN2)) segment 6, complete sequence, 2006.
Jan. 29, 2009 Office Action and Notice of References Cited in parent U.S. Appl. No. 12/156,456.
Response to Jan. 29, 2009 Office Action in parent U.S. Appl. No. 12/156,456.
Oct. 20, 2009 Office Action and Notice of References Cited in parent U.S. Appl. No. 12/156,456.
Bragstad, et al., Pandemic influenza 1918 H1N1 and 1968 H3N2 DNA vaccines induce cross-reactive immunity in ferrets against infection with viruses drifted for decades, Influenza and Other Respiratory Viruses, Nov. 3, 2010, pp. 13-23, vol. 5.
Drape, et al., Epidermal DNA vaccine for influenza is immunogenic in humans, Vaccine, Aug. 19, 2005, pp. 4475-4481, vol. 24.
Jones, et al., DNA vaccination protects against an influenza challenge in a double-blind randomised placebo-controlled phase 1b clinical trial, Vaccine, Feb. 24, 2009, pp. 2506-2512, vol. 27.
Kutzler and Weiner, DNA vaccines: ready for prime time?, Nature Reviews, Genetics, Oct. 2008, pp. 776-788, vol. 9.

* cited by examiner

Days after viral challenge

Specific IgG titre

RNA copies

Days after viral challenge

- HA and NA 1918 H1N1 DNA
- HA, NA, NP and M2 1918 H1N1 DNA
- Empty plasmid
- HA and NA H1N1 A/New Caledonia/20/99 DNA

SEQUENCE LISTING

```
<160> NUMBER OF SEQ ID NOS: 21

<210> SEQ ID NO 1
<211> LENGTH: 1701
<212> TYPE: DNA
<213> ORGANISM: Artificial
<220> FEATURE:
```

-continued

<223> OTHER INFORMATION: HA 1918 synthetic gene 0607838; A/South Carolina/1/18

<400> SEQUENCE: 1

```
atggaggcca ggctgctggt gctgctgtgc gccttcgccg ccaccaacgc cgacaccatc     60
tgcatcggct accacgccaa caacagcacc gacaccgtgg ataccgtgct ggagaagaac    120
gtgaccgtga cccacagcgt gaacctgctg gaggacagcc acaacggcaa gctgtgcaag    180
ctgaagggaa tcgctcccct gcagctgggc aagtgcaaca tcgccggctg gctgctgggc    240
aaccccgagt gcgacctgct gctgaccgcc agcagctggt cctacatcgt ggagaccagc    300
aacagcgaga acggcacctg ctaccccggc gacttcatcg actacgagga gctgcgggag    360
cagctgtcca gcgtgagcag cttcgagaag ttcgagatct tccccaagac cagctcctgg    420
cccaaccacg agaccaccaa gggcgtgacc gccgcctgta gctacgccgg agccagcagc    480
ttctacagaa acctgctgtg gctgaccaag aagggcagca gctaccccaa gctgtccaag    540
agctacgtga acaacaaggg caaggaagtg ctggtgctgt ggggcgtgca ccaccccccct   600
accggcaccg accagcagag cctgtaccag aacgccgacg cctacgtgag cgtgggcagc    660
agcaagtaca acagaaggtt cacccccgag atcgccgcca ggcccaaggt gcgcgaccag    720
gccggcagga tgaactacta ctggaccctg ctggagcccg gcgacaccat caccttcgag    780
gccaccggca acctgatcgc cccttggtac gccttcgccc tgaacagggg cagcggcagc    840
ggcatcatca ccagcgacgc ccccgtgcac gactgcaaca ccaagtgcca gacccccccac   900
ggagccatca acagcagcct gcccttccag aacatccacc ccgtgaccat cggcgagtgc    960
cccaagtacg tgagaagcac caagctgagg atggccaccg gcctgaggaa catccccagc   1020
atccagagca ggggcctgtt cggagccatc gccggattca tcgagggcgg ctggaccggc   1080
atgatcgacg gctggtacgg ctaccaccac cagaacgagc agggcagcgg ctacgccgcc   1140
gaccagaaga gcacccagaa cgccatcgac ggcatcacca acaaggtgaa cagcgtgatc   1200
gagaagatga acacccagtt caccgccgtg ggcaaggagt tcaacaacct ggagaggcgg   1260
atcgagaacc tgaacaagaa ggtggacgac ggcttcctgg acatctggac ctacaacgcc   1320
gagctgctgg tgctgctgga gaacgagagg accctggact tccacgacag caacgtgagg   1380
aacctgtacg agaaggtgaa gagccagctg aagaacaacg ccaaggagat cggcaacggc   1440
tgcttcgagt tctaccacaa gtgcgacgac gcctgcatgg agagcgtgag aaacggcacc   1500
tacgactacc ccaagtacag cgaggagagc aagctgaacc gggaggagat cgacggcgtg   1560
aagctggaga gcatgggcgt gtaccagatc ctggccatct acagcaccgt ggccagcagc   1620
ctggtgctgc tggtgtccct gggagccatc agcttttgga tgtgcagcaa cggcagcctg   1680
cagtgcagga tctgcatctg a                                              1701
```

<210> SEQ ID NO 2
<211> LENGTH: 566
<212> TYPE: PRT
<213> ORGANISM: Artificial
<220> FEATURE:
<223> OTHER INFORMATION: HA 1918 synthetic gene 0607838; A/South Carolina/1/18

<400> SEQUENCE: 2

```
Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460
```

-continued

```
Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 3
<211> LENGTH: 1410
<212> TYPE: DNA
<213> ORGANISM: Artificial
<220> FEATURE:
<223> OTHER INFORMATION: HA 1918 synthetic gene 0607869; A/Brevig
      mission/1/1918

<400> SEQUENCE: 3

atgaacccca accagaagat catcaccatc ggcagcatct gcatggtggt gggcatcatc      60

agcctgatcc tgcagatcgg caacatcatc agcatctggg tgtcccacag catccagacc     120

ggcaaccaga accaccccga gacctgcaac cagtccatca tcacctacga gaacaacacc     180

tgggtgaacc agacctacgt gaacatcagc aacaccaacg tggtggccgg ccaggacgcc     240

acctccgtga tcctgacagg caacagcagc ctgtgcccca tcagcggctg ggccatctac     300

agcaaggaca acggcatcag gatcggcagc aagggcgacg tgttcgtgat cagagagccc     360

ttcatcagct gcagccacct ggaatgcagg accttcttcc tgacccaagg agccctgctg     420

aacgacaagc acagcaacgg caccgtgaag gacagaagcc cctacaggac cctgatgagc     480

tgccccgtgg gcgaggctcc cagcccctac aacagcagat tcgagagcgt ggcctggtcc     540

gccagcgcct gccacgacgg catgggctgg ctgaccatcg gcatcagcgg ccctgacaac     600

ggggccgtgg ccgtgctgaa gtacaacgga atcatcaccg acaccatcaa gagctggcgg     660

aacaacatcc tgaggaccca ggaaagcgag tgcgcctgcg tgaacggcag ctgcttcacc     720

atcatgaccg acggccccag caacggccag gccagctaca agatcctgaa gatcgagaag     780

ggcaaggtga ccaagagcat cgagctgaac gcccccaact accactacga ggaatgcagc     840

tgctaccccg acaccggcaa ggtcatgtgc gtgtgcaggg acaactggca cggcagcaac     900

aggccctggg tgtccttcga ccagaacctg gactaccaga tcggatacat ctgcagcggc     960

gtgttcggcg acaaccccag gcccaacgac ggcaccggca gctgcggccc tgtgagcagc    1020

aacggggcca atggcatcaa gggcttcagc ttcagatacg acaacggcgt gtggatcggc    1080

cgcaccaaga gcaccagcag cagatccggc ttcgagatga tctgggaccc caacggctgg    1140

accgagaccg acagcagctt cagcgtgagg caggacatcg tggccatcac cgactggtcc    1200

ggctacagcg gcagcttcgt gcagcacccc gagctgaccg gcctggactg catgaggccc    1260

tgtttctggg tggagctgat cagaggccag cccaaggaga acaccatctg gaccagcggc    1320

agcagcatca gcttttgcgg cgtgaacagc gacaccgtgg gctggtcctg gcccgacggg    1380

gccgagctgc ccttcagcat cgataagtga                                     1410
```

<210> SEQ ID NO 4
<211> LENGTH: 469
<212> TYPE: PRT
<213> ORGANISM: Artificial
<220> FEATURE:
<223> OTHER INFORMATION: HA 1918 synthetic gene 0607869; A/Brevig mission/1/1918

<400> SEQUENCE: 4

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Val Ser His Ser Ile Gln Thr Gly Asn Gln Asn His Pro Glu Thr
        35                  40                  45

Cys Asn Gln Ser Ile Ile Thr Tyr Glu Asn Asn Thr Trp Val Asn Gln
    50                  55                  60

Thr Tyr Val Asn Ile Ser Asn Thr Asn Val Val Ala Gly Gln Asp Ala
65                  70                  75                  80

Thr Ser Val Ile Leu Thr Gly Asn Ser Ser Leu Cys Pro Ile Ser Gly
                85                  90                  95

Trp Ala Ile Tyr Ser Lys Asp Asn Gly Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asn Gly Gln Ala Ser Tyr Lys Ile Leu
                245                 250                 255

Lys Ile Glu Lys Gly Lys Val Thr Lys Ser Ile Glu Leu Asn Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Gly Ser Asn Arg Pro Trp Val
    290                 295                 300

Ser Phe Asp Gln Asn Leu Asp Tyr Gln Ile Gly Tyr Ile Cys Ser Gly
305                 310                 315                 320

Val Phe Gly Asp Asn Pro Arg Pro Asn Asp Gly Thr Gly Ser Cys Gly
                325                 330                 335

Pro Val Ser Ser Asn Gly Ala Asn Gly Ile Lys Gly Phe Ser Phe Arg
            340                 345                 350

Tyr Asp Asn Gly Val Trp Ile Gly Arg Thr Lys Ser Thr Ser Ser Arg
        355                 360                 365
```

```
Ser Gly Phe Glu Met Ile Trp Asp Pro Asn Gly Trp Thr Glu Thr Asp
    370                 375                 380

Ser Ser Phe Ser Val Arg Gln Asp Ile Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Gln Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Ser Ile Asp Lys
465


<210> SEQ ID NO 5
<211> LENGTH: 1497
<212> TYPE: DNA
<213> ORGANISM: Artificial
<220> FEATURE:
<223> OTHER INFORMATION: HA 1918 synthetic gene 0607866; A/Brevig
      mission/1/1918

<400> SEQUENCE: 5

atggccagcc agggcaccaa gagaagctac gagcagatgg aaaccgacgg cgagaggcag     60

aacgccaccg agatcagggc cagcgtgggc aggatgatcg gcggcatcgg caggttctac    120

atccagatgt gcaccgagct gaagctgtcc gactacgagg gcaggctgat ccagaacagc    180

atcaccatcg agaggatggt gctgtccgcc ttcgacgaga gaagaaacaa gtacctggaa    240

gagcacccca gcgccggcaa ggaccccaag aaaaccggcg gacccatcta cagaaggatc    300

gacggcaagt ggatgagaga gctgatcctg tacgacaagg aggaaatcag aaggatctgg    360

cggcaggcca acaacggcga ggacgccaca gccggcctga cccacatgat gatctggcac    420

agcaacctga acgacgccac ctaccagagg accagggccc tcgtcagaac cggcatggac    480

ccccggatgt gcagcctgat gcagggcagc acactgccca gaagaagcgg agctgctgga    540

gccgccgtga agggcgtggg caccatggtg atggaactga tcaggatgat caagaggggc    600

atcaacgaca ggaacttttg gaggggcgag aacggcagaa ggaccaggat cgcctacgag    660

aggatgtgca acatcctgaa gggcaagttc cagacagccg cccagagggc catgatggac    720

caggtccggg agagcaggaa ccccggcaac gccgagatcg aggacctgat cttcctggcc    780

agaagcgccc tgatcctgag gggcagcgtg gcccacaaga gctgcctgcc cgcctgcgtg    840

tacggacccg ccgtggccag cggctacgac ttcgagagag agggctacag cctggtcggc    900

atcgacccct tcaggctgct gcagaactcc caggtgtact ctctgatcag gcccaacgag    960

aaccccgccc acaagtccca gctggtctgg atggcctgcc acagcgccgc cttcgaggat   1020

ctgagagtga gcagcttcat caggggcacc agagtggtgc ccaggggcaa gctgtccacc   1080

aggggcgtgc agatcgccag caacgagaac atggaaacca tggacagcag caccctggaa   1140

ctgagaagca ggtactgggc catcaggacc agaagcggcg gcaacaccaa ccagcagagg   1200

gccagcgccg gacagatcag cgtgcagccc accttctccg tgcagaggaa cctgcccttc   1260

gagagggcca ccatcatggc cgccttcacc ggcaacaccg agggcaggac cagcgacatg   1320

aggaccgaga tcatcagaat gatggaaagc gccaggcccg aggacgtgag cttccagggc   1380

aggggcgtgt tcgagctgtc cgatgagaag gccacctccc ccatcgtgcc cagcttcgac   1440
```

atgagcaacg agggcagcta cttcttcggc gacaacgccg aggaatacga caactga 1497

<210> SEQ ID NO 6
<211> LENGTH: 498
<212> TYPE: PRT
<213> ORGANISM: Artificial
<220> FEATURE:
<223> OTHER INFORMATION: HA 1918 synthetic gene 0607866; A/Brevig mission/1/1918

<400> SEQUENCE: 6

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350
```

```
Val Pro Arg Gly Lys Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 7
<211> LENGTH: 988
<212> TYPE: DNA
<213> ORGANISM: Artificial
<220> FEATURE:
<223> OTHER INFORMATION: HA 1918 synthetic gene 0607868; A/Brevig
      mission/1/1918

<400> SEQUENCE: 7

atgagtcttt taaccgaggt cgaaacgtac gttctctcta tcgtcccgtc aggccccctc     60

aaagccgaga tcgcgcagag acttgaagat gtctttgcag ggaagaacac cgatcttgag    120

gctctcatgg aatggctaaa gacaagacca atcctgtcac ctctgactaa ggggatttta    180

ggatttgtgt tcacgctcac cgtgcccagt gagcgaggac tgcagcgtag acgctttgtc    240

caaaatgccc ttaatgggaa cggggatcca aataacatgg acagagcagt taaactgtac    300

aggaagctta agagggagat aacattccat ggggccaaag aagtagcact cagttattcc    360

gctggtgcac ttgccagttg tatgggcctc atatacaaca ggatggggac tgtgaccact    420

gaagtggcat ttggcctggt atgcgcaacc tgtgaacaga ttgctgattc ccagcatcgg    480

tctcacaggc aaatggtgac aacaaccaat ccactaatca gacatgagaa cagaatggta    540

ctggccagca ctacggctaa ggctatggag caaatggctg gatcgagtga gcaagcagca    600

gaggccatgg aggttgctag tcaggctagg caaatggtgc aggcgatgag aaccattggg    660

actcatccta gctccagtgc tggtctgaaa gacgatctta ttgaaaattt gcaggcctac    720

cagaaacgaa tgggggtgca gatgcaacga ttcaagtgat cctctcgtta ttgccgcaag    780

tatcattggg atcttgcact tgatattgtg gattcttgat cgtctttttt tcaaatgcat    840

ttatcgtcgc cttaaatacg gtttgaaaag agggccttct acggaaggag tgccggagtc    900

tatgagggaa gaatatcgaa aggaacagca gagtgctgtg gatgttgacg atggtcattt    960

tgtcaacata gagctggagt aaggcgcc                                        988


<210> SEQ ID NO 8
<211> LENGTH: 252
<212> TYPE: PRT
<213> ORGANISM: Artificial
<220> FEATURE:
```

<223> OTHER INFORMATION: HA 1918 synthetic gene 0607868; A/Brevig mission/1/1918

<400> SEQUENCE: 8

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Ile Glu Asn Leu Gln Ala Tyr
225                 230                 235                 240

Gln Lys Arg Met Gly Val Gln Met Gln Arg Phe Lys
                245                 250
```

<210> SEQ ID NO 9
<211> LENGTH: 97
<212> TYPE: PRT
<213> ORGANISM: Artificial
<220> FEATURE:
<223> OTHER INFORMATION: HA 1918 synthetic gene 0607868; A/Brevig mission/1/1918

<400> SEQUENCE: 9

```
Met Ser Leu Leu Thr Glu Val Glu Thr Pro Thr Arg Asn Glu Trp Gly
1               5                   10                  15

Cys Arg Cys Asn Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Val Asp Asp Gly His Phe Val Asn Ile Glu Leu
```

-continued 85 90 95

Glu

<210> SEQ ID NO 10
<211> LENGTH: 1731
<212> TYPE: DNA
<213> ORGANISM: Artificial
<220> FEATURE:
<223> OTHER INFORMATION: HA H3N2 A/Aichi/2/1968(H3N2)

<400> SEQUENCE: 10

```
ataattctat taatcatgaa gaccatcatt gctttgagct acattttctg tctggctctc     60

ggccaagacc ttccaggaaa tgacaacagc acagcaacgc tgtgcctggg acatcatgcg    120

gtgccaaacg gaacactagt gaaaacaatc acagatgatc agattgaagt gactaatgct    180

actgagctag ttcagagctc ctcaacgggg aaaatatgca acaatcctca tcgaatcctt    240

gatggaatag actgcacact gatagatgct ctattggggg accctcattg tgatgttttt    300

caaaatgaga catgggacct tttcgttgaa cgcagcaaag ctttcagcaa ctgttaccct    360

tatgatgtgc cagattatgc ctcccttagg tcactagttg cctcgtcagg cactctggag    420

tttatcactg agggtttcac ttggactggg gtcactcaga atgggggaag caatgcttgc    480

aaaaggggac ctggtagcgg tttttttcagt agactgaact ggttgaccaa atcaggaagc    540

acatatccag tgctgaacgt gactatgcca aacaatgaca attttgacaa actatacatt    600

tggggggttc accacccgag cacgaaccaa gaacaaacca gcctgtatgt tcaagcatca    660

gggagagtca cagtctctac caggagaagc cagcaaacta taatcccgaa tatcgagtcc    720

agaccctggg taaggggtct gtctagtaga ataagcatct attggacaat agttaagccg    780

ggagacgtac tggtaattaa tagtaatggg aacctaatcg ctcctcgggg ttatttcaaa    840

atgcgcactg ggaaaagctc aataatgagg tcagatgcac ctattgatac ctgtatttct    900

gaatgcatca ctccaaatgg aagcattccc aatgacaagc cctttcaaaa cgtaaacaag    960

atcacatatg gagcatgccc caagtatgtt aagcaaaaca ccctgaagtt ggcaacaggg   1020

atgcggaatg taccagagaa acaaactaga ggcctattcg gcgcaatagc aggtttcata   1080

gaaaatggtt gggagggaat gatagacggt tggtacggtt tcaggcatca aaattctgag   1140

ggcacaggac aagcagcaga tcttaaaagc actcaagcag ccatcgacca aatcaatggg   1200

aaattgaaca gggtaatcga gaagacgaac gagaaattcc atcaaatcga aaaggaattc   1260

tcagaagtag aagggagaat tcaggacctc gagaaatacg ttgaagacac taaaatagat   1320

ctctggtctt acaatgcgga gcttcttgtc gctctggaga atcaacatac aattgacctg   1380

actgactcgg aaatgaacaa gctgtttgaa aaaacaagga ggcaactgag ggaaaatgct   1440

gaagacatgg gcaatggttg cttcaaaata taccacaaat gtgacaacgc ttgcatagag   1500

tcaatcagaa atgggactta tgaccatgat gtatacagag acgaagcatt aaacaaccgg   1560

tttcagatca aaggtgttga actgaagtct ggatacaaag actggatcct gtggatttcc   1620

tttgccatat catgcttttt gctttgtgtt gttttgctgg ggttcatcat gtgggcctgc   1680

cagagaggca acattaggtg caacatttgc atttgagtgt attagtaatt a            1731
```

<210> SEQ ID NO 11
<211> LENGTH: 566
<212> TYPE: PRT
<213> ORGANISM: Artificial
<220> FEATURE:
<223> OTHER INFORMATION: HA H3N2 A/Aichi/2/1968(H3N2)

<400> SEQUENCE: 11

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565
```

<210> SEQ ID NO 12
<211> LENGTH: 1431
<212> TYPE: DNA
<213> ORGANISM: Artificial
<220> FEATURE:
<223> OTHER INFORMATION: HA H3N2 A/Aichi/2/1968(H3N2)

<400> SEQUENCE: 12

```
gaaaatgaat ccaaatcaaa agataataac aattggctct gtctctctca ccattgcaac     60

agtatgcttc ctcatgcaga ttgccatcct ggtaactact gtaacattgc attttaagca    120

atatgagtgc gactcccccg cgagcaacca agtaatgccg tgtgaaccaa taataataga    180

aaggaacata acagagatag tgtatttgaa taacaccacc atagagaaag agatatgccc    240

caaagtagtg gaatacagaa attggtcaaa gccgcaatgt caaattacag gatttgcacc    300

tttttctaag gacaattcaa tccggctttc tgctggtggg gacatttggg tgacgagaga    360

accttatgtg tcatgcgatc atggcaagtg ttatcaattt gcactcgggc aggggaccac    420

actagacaac aaacattcaa atgacacaat acatgataga atccctcatc gaaccctatt    480

aatgaatgag ttgggtgttc catttcattt aggaaccagg caagtgtgta tagcatggtc    540

cagctcaagt tgtcacgatg gaaaagcatg gctgcatgtt tgtatcactg gggatgacaa    600

aaatgcaact gctagcttca tttatgacgg gaggcttgtg gacagtattg gttcatggtc    660

tcaaaatatc ctcagaaccc aggagtcgga atgcgtttgt atcaatggga cttgcacagt    720

agtaatgact gatggaagtg cttcaggaag agccgatact agaatactat tcattgaaga    780

ggggaaaatt gtccatatta gcccattgtc aggaagtgct cagcatgtag aagagtgttc    840

ctgttatcct agatatcctg gcgtcagatg tatctgcaga gacaactgga aaggctctaa    900

taggcccgtc gtagacataa atatggaaga ttatagcatt gattccagtt atgtgtgctc    960

agggcttgtt ggcgacacac ctagaaacga cgacagatct agcaatagca attgcaggaa   1020

tcctaataat gagagaggga atcaaggagt gaaaggctgg gcctttgaca atggagatga   1080

cgtgtggatg ggaagaacga tcagcaagga tttacgctca ggttatgaaa ctttcaaagt   1140

cattggtggt tggtccacac ctaattccaa atcgcagatc aatagacaag tcatagttga   1200
```

-continued

```
cagcgataat cggtcaggtt actctggtat tttctctgtt gagggcaaaa gctgcatcaa   1260

taggtgcttt tatgtggagt tgataagggg aaggaaacag gagactagag tgtggtggac   1320

ctcaaacagt attgttgtgt tttgtggcac ttcaggtacc tatggaacag gctcatggcc   1380

tgatggggcg aacatcaatt tcatgcctat ataagctttc gcaattttag a            1431


<210> SEQ ID NO 13
<211> LENGTH: 469
<212> TYPE: PRT
<213> ORGANISM: Artificial
<220> FEATURE:
<223> OTHER INFORMATION: HA H3N2 A/Aichi/2/1968(H3N2)

<400> SEQUENCE: 13

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln Tyr Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Lys
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335
```

```
Cys Arg Asn Pro Asn Asn Glu Arg Gly Asn Gln Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 14
<211> LENGTH: 1733
<212> TYPE: DNA
<213> ORGANISM: Artificial
<220> FEATURE:
<223> OTHER INFORMATION: HA H2N2 A/Albany/20/1957(H2N2)

<400> SEQUENCE: 14
atagacaacc aaaagcaaaa caatggccat catttatctc attctcctgt tcacagcagt      60
gagaggggac cagatatgca ttggatacca tgccaataat tccacagaga aggtcgacac     120
aattctagag cggaacgtca ctgtgactca tgccaaggac attcttgaga agacccataa     180
cggaaagtta tgcaaactaa acggaatccc tccacttgaa ctaggggact gtagcattgc     240
cggatggctc cttggaaatc cagaatgtga taggcttcta agtgtgccag aatggtccta     300
tataatggag aaagaaaacc cgagagacgg tttgtgttat ccaggcagct tcaatgatta     360
tgaagaattg aaacatctcc tcagcagcgt gaaacatttc gagaaagtaa agattctgcc     420
caaagataga tggacacagc atacaacaac tggaggttca cgggcctgcg cggtgtctgg     480
taatccatca ttcttcagga acatgatctg gctgacaaag aaaggatcaa attatccggt     540
tgccaaagga tcgtacaaca atacaagcgg agaacaaatg ctaataattt ggggggtgca     600
ccatcccaat gatgagacag aacaaagaac attgtaccag aatgtgggaa cctatgtttc     660
cgtaggcaca tcaacattga acaaaaggtc aaccccagac atagcaacaa ggcctaaagt     720
gaatggacta ggaagtagaa tggaattctc ttggacccta ttggatatgt gggacaccat     780
aaattttgag agtactggta atctaattgc accagagtat ggattcaaaa tatcgaaaag     840
aggtagttca gggatcatga aaacagaagg aacacttggg aactgtgaga ccaaatgcca     900
aactcctttg ggagcaataa atacaacatt gccttttcac aatgtccacc cactgacaat     960
aggtgagtgc cccaaatatg taaaatcgga gaagttggtc ttagcaacag gactaaggaa    1020
tgttccccag attgaatcaa gaggattgtt tggggcaata gctggtttta tagaaggagg    1080
atggcaagga atggttgatg gttggtatgg ataccatcac agcaatgacc agggatcagg    1140
gtatgcagcg gacaaagaat ccactcaaaa ggcatttgat ggaatcacca acaaggtaaa    1200
ttctgtgatt gaaaagatga acacccaatt tgaagctgtt gggaaagaat tcagtaactt    1260
```

-continued

```
agagagaaga ctggagaact tgaacaaaaa gatggaagac gggtttctag atgtgtggac   1320

atacaatgct gagcttctag ttctgatgga aaatgagagg acacttgact ttcatgattc   1380

taatgtcaag aatctgtatg ataaagtcag aatgcagctg agagacaacg tcaaagaact   1440

aggaaatgga tgttttgaat tttatcacaa atgtgatgat gaatgcatga atagtgtgaa   1500

aaacgggacg tatgattatc ccaagtatga agaagagtct aaactaaata gaaatgaaat   1560

caaaggggta aaattgagca gcatgggggt ttatcaaatc cttgccattt atgctacagt   1620

agcaggttct ctgtcactgg caatcatgat ggctgggatc tctttctgga tgtgctccaa   1680

cgggtctctg cagtgcagga tctgcatatg attataagtc attttataat taa          1733
```

<210> SEQ ID NO 15
<211> LENGTH: 562
<212> TYPE: PRT
<213> ORGANISM: Artificial
<220> FEATURE:
<223> OTHER INFORMATION: HA H2N2 A/Albany/20/1957(H2N2)

<400> SEQUENCE: 15

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Ile Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Gly Asn Cys
        275                 280                 285
```

```
Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 16
<211> LENGTH: 1435
<212> TYPE: DNA
<213> ORGANISM: Artificial
<220> FEATURE:
<223> OTHER INFORMATION: HA H2N2 A/Albany/20/1957(H2N2)

<400> SEQUENCE: 16

tgaaaatgaa tccaaatcaa aagataataa caattggctc tgtctctctc accattgcaa      60

cagtatgctt cctcatgcag attgccatcc tggcaactac tgtgacattg cattttaaac     120

aacatgagtg cgactccccc gcgagcaacc aagtaatgcc atgtgaacca ataataatag     180

aaaggaacat aacagagata gtgtatttga ataacaccac catagagaaa gagatttgcc     240

ccgaagtagt ggaatacaga aattggtcaa agccgcaatg tcaaattaca ggatttgcac     300

ctttttctaa ggacaattca atccggcttt ctgctggtgg ggacatttgg gtgacgagag     360

aaccttatgt gtcatgcgat cctggcaagt gttatcaatt tgcactcggg caagggacca     420

cactagacaa caaacattca aatggcacaa tacatgatag aatccctcac cgaaccctat     480

taatgaatga gttgggtgtt ccatttcatt taggaaccaa acaagtgtgt gtagcatggt     540
```

```
ccagctcaag ttgtcacgat ggaaaagcat ggttgcatgt ttgtgtcact ggggatgata    600

gaaatgcgac tgccagcttc atttatgacg ggaggcttgt ggacagtatt ggttcatggt    660

ctcaaaatat cctcaggacc caggagtcgg aatgcgtttg tatcaatggg acttgcacag    720

tagtaatgac tgatggaagt gcatcaggaa gagccgatac tagaatacta ttcattaaag    780

aggggaaaat tgtccatatc agcccattgt caggaagtgc tcagcatata gaggagtgtt    840

cctgttaccc tcgatatcct gacgtcagat gtatctgcag agacaactgg aaaggctcta    900

ataggcccgt tatagacata aatatggaag attatagcat tgattccagt tatgtgtgct    960

cagggcttgt tggcgacaca cccaggaacg acgacagctc tagcaatagc aattgcaggg   1020

atcctaacaa tgagagaggg aatccaggag tgaaaggctg ggcctttgac aatggagatg   1080

atgtatggat gggaagaaca atcaacaaag attcacgctc aggttatgaa actttcaaag   1140

tcattggtgg ttggtccaca cctaattcca aatcgcaggt caatagacag gtcatagttg   1200

acaacaataa ttggtctggt tactctggta ttttctctgt tgagggcaaa agctgcatca   1260

ataggtgctt ttatgtggag ttgataaggg gaaggccaca ggagactaga gtatggtgga   1320

cctcaaacag tattgttgtg ttttgtggca cttcaggtac ttatggaaca ggctcatggc   1380

ctgatggggc gaacatcaat ttcatgccta tataagcttt cgcaatttta gaaaa        1435
```

<210> SEQ ID NO 17
<211> LENGTH: 469
<212> TYPE: PRT
<213> ORGANISM: Artificial
<220> FEATURE:
<223> OTHER INFORMATION: HA H2N2 A/Albany/20/1957(H2N2)

<400> SEQUENCE: 17

```
Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Ala Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Glu
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asp Asn Lys His
    130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Val
                165                 170                 175

Ala Trp Ser Ser Ser Ser Cys His Asp Gly Lys Ala Trp Leu His Val
            180                 185                 190

Cys Val Thr Gly Asp Asp Arg Asn Ala Thr Ala Ser Phe Ile Tyr Asp
        195                 200                 205
```

```
Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Lys Glu Gly Lys Ile Val His Ile Ser Pro Leu Ser Gly Ser Ala
            260                 265                 270

Gln His Ile Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Ser Ser Ser Asn Ser Asn
                325                 330                 335

Cys Arg Asp Pro Asn Asn Glu Arg Gly Asn Pro Gly Val Lys Gly Trp
            340                 345                 350

Ala Phe Asp Asn Gly Asp Asp Val Trp Met Gly Arg Thr Ile Asn Lys
        355                 360                 365

Asp Ser Arg Ser Gly Tyr Glu Thr Phe Lys Val Ile Gly Gly Trp Ser
    370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Pro Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465


<210> SEQ ID NO 18
<211> LENGTH: 33
<212> TYPE: DNA
<213> ORGANISM: Artificial
<220> FEATURE:
<223> OTHER INFORMATION: 1918 H1N1 construct

<400> SEQUENCE: 18

caacgcgtgc caccatgaaa gcaaaactac tgg                                33


<210> SEQ ID NO 19
<211> LENGTH: 30
<212> TYPE: DNA
<213> ORGANISM: Artificial
<220> FEATURE:
<223> OTHER INFORMATION: 1918 H1N1 construct

<400> SEQUENCE: 19

tcggcgcctc agatgcatat tctacactgc                                    30


<210> SEQ ID NO 20
<211> LENGTH: 27
<212> TYPE: DNA
<213> ORGANISM: Artificial
```

-continued

```
<220> FEATURE:
<223> OTHER INFORMATION: 1918 H1N1 construct

<400> SEQUENCE: 20

caacgcgtgc caccatgaat ccaaatc                                       27


<210> SEQ ID NO 21
<211> LENGTH: 30
<212> TYPE: DNA
<213> ORGANISM: Artificial
<220> FEATURE:
<223> OTHER INFORMATION: 1918 H1N1 construct

<400> SEQUENCE: 21

tcggcgccct acttgtcaat ggtgaacggc                                    30
```

INFLUENZA VACCINES

CROSS-REFERENCE TO RELATED APPLICATIONS

This application is a division of U.S. patent application Ser. No. 12/156,456, filed May 30, 2008, which claims the benefit under 35 USC 119(e) of U.S. Patent Application No. 60/934,117, filed Jun. 11, 2007.

BACKGROUND OF THE INVENTION

The invention concerns therapeutic and prophylactic vaccines for humans and swine, for influenza A infections in humans and swine.

Influenza is one of the oldest and most common diseases known to man, causing between three and five million cases of severe illness and between 250,000 and 500,000 deaths every year around the world. Also, swine are susceptible to human and avian influenza virus, since they possess both receptors in their respiratory tract. Because swine get infection and pneumonia from human influenza strains, they may serve as a dangerous mixing vessel for the generation of new recombinant influenza strains with pandemic potential.

Influenza rapidly spreads in seasonal epidemics affecting 5-15% of the population and the burden on health care costs and lost productivity are extensive (World Health Organization (WHO)). Influenza like illness was first described by Hippocrates in the year 412 BC. Up to the 19th century, influenza was thought to be a bacterial infection. Virus as the causative agent was first determined in 1931 by Richard Shope. The first known influenza A pandemic was in 1580. Since then there have been 31 pandemics of which three appeared in the 20th century, namely the 'Spanish flu' in 1918, the 'Asian flu' in 1957 and the 'Hong Kong flu' in 1968, respectively. The pandemic of 1918 influenza A H1N1 was the worst pandemic in recent times causing 20 to 50 million deaths worldwide. Influenza most commonly presents as seasonal outbreaks and epidemics of variable severity.

Zoonosis of avian influenza virus (MV) able to infect humans and swine and its spread in Asia, parts of Europe and the Middle East has recently evoked the concern about a pandemic occurring also in the $21^{st}$ century. The causative strain of such a pandemic will probably be unknown until the pandemic emerges, at which time there will be an urgent need for a vaccine. Therefore, fast diagnosis and characterisation of circulating strains as well as emerging strains, new alternative vaccines approaches and production methods will be required in order to minimise the severity of the pandemic.

Since seasonal influenza A vaccines are produced on eggs, an epidemic of highly pathogenic AIV among poultry will also influence the production of seasonal vaccines. Moreover, the traditional influenza protein vaccines only have a limited protective effect. Also, seasonal vaccines have to be changed every season because of the genetic drift of influenza A virus and the narrow type specific antibody induction by traditional influenza A protein vaccines. Therefore, there is a need for new alternative influenza A vaccines with different properties.

The influenza virus belongs to the Orthomyxoviridae family. The family includes three genera; influenza A, B and C viruses, identified by antigenic differences in their nucleoprotein (NP) and matrix protein (M). The influenza A genus is further divided into subtype combinations based on the antigenic differences of the surface glycoproteins hemagglutinin (HA) and neuraminidase (NA). The A strain has evolved to be able to infect several other mammalian species (e.g. horses and swine). Influenza A viruses of all recognised 16 HAs and 9 NAs antigenic subtypes have been recovered from aquatic birds, but few infect other animal species which indicates that aquatic birds are the natural reservoirs of influenza A.

The influenza A viruses have been the causative agents for the major pandemics and most of the annual outbreaks of epidemic influenza. The current nomenclature system for human influenza viruses includes the geographical location of first isolation, strain number, and year of isolation. The antigenic description of HA and NA is given in brackets, e.g., A/Moscow/10/99 (H3N2). Nonhuman strains also include the host of origin in the nomenclature, e.g., A/mallard/Denmark/64650/03(H5N7).

The influenza A virus genome consist of eight negative sense single stranded (ss) ribonucleic acid (RNA) segments packed in the viral core comprised of host cell membrane and a matrix 1 (M1) protein layer. The eight segments are associated with nucleoprotein (NP) and three large proteins; polymerase basic 1 (PB1) and 2 (PB2) protein, and polymerase acidic (PA) protein, which are responsible for RNA replication and transcription. NP encapsulates the RNA and forms ribonucleoprotein (RNP) complexes that protect and stabilise the RNA. Each segment include a sequence of 11-13 nucleotides at the 5' ends and 9-12 nucleotides at the 3' ends which are highly conserved and similar for A, B and C viruses. The major glycoproteins HA and NA, and the ion channel M2 protein, are embedded in a host derived lipid bilayer. Influenza viruses are somewhat pleomorphic in shape, but mostly spherical (80-120 nm in diameter).

All subtypes of influenza A are perpetuated in the wild aquatic bird population, believed to be the natural reservoir of influenza. Under normal circumstances an influenza infection in wild ducks is asymptomatic. The virus replicates in the intestinal tract and is excreted in high concentrations with the feces for a period up to 30 days. An avian influenza virus can persist in water and retain infectivity for about 100 days at 17° C. and can be stored indefinitely at −50° C. The continuous circulation of influenza A viruses might be due to bird overwintering sites in the subtropics. The 2004H5N1 strains have become very stable and can survive for 6 days at 37° C. The virus is killed by heat at 56° C. for 3 hours or 60° C. for 30 minutes. Disinfectants like formalin and iodine compounds can also efficiently kill the influenza virus. Avian influenza viruses have been believed to be in evolutionary stasis in its natural host, the virus and the host tolerate each other. Generally no severe clinical symptoms are seen when poultry are infected with avian influenza, and the virus is described as a low pathogenic avian influenza virus (LP AIV). The subtypes H5 and H7 have the potential to become highly pathogenic (HP) to chickens through accumulation of mutations after transmission to poultry. Contrary to previous belief, wild migratory birds might play some role in the transmission of HP AIV. Thousands of wild aquatic birds in Hong Kong 2002 and China 2005 became infected with HP AIV H5N1 and this contributed to the spread of HP H5N1 to Europe and Africa in 2005.

Seasonal influenza strains have been isolated from humans and swine all year round. However, in temperate climates it is a winter disease, probably because people come together and stay in less ventilated rooms due to the cold weather.

Of the 16 recognised subtypes of HA and 9 NAs, only H1, H2, H3, N1 and N2 have circulated in humans and swine in the last century. The pandemic introduction in humans of these types were 1918 H1N1, 1957H2N2 ("Asiatic flu"), 1968 H3N2 ("HongKong Flu") and non-pandemic introduction of the reassorted new type H1N2 in 2001, respectively. The antigenicity of human influenza viruses are constantly changing by accumulation of mutations in the HA and NA antigenic sites, thereby making the virus capable of evading the host immune system causing epidemics. Viral mutagenesis is enhanced by the lack of "proof reading" in the replication of RNA. The mutation frequency is approximately one in 100,000 nucleotides. In the northern hemisphere seasonal influenza outbreaks usually occur between October and April. In the southern hemisphere, these outbreaks usually occur between April and October. The antigenic drift of human influenza viruses is closely monitored by WHO's global influenza surveillance program. The components of the next seasons' influenza vaccine for the northern hemisphere is determined in February based on the knowledge about the current circulating strains, and re-evaluated in September for the southern hemisphere.

Antigenic shift can occur in three ways. Either by direct transmission of an avian strain adapted to humans, genetic reassortment or reintroduction of an "old" strain. The possibility of an avian influenza virus crossing the species barrier and infecting humans directly was not recognised before 1997 when 18 people in Hong Kong became ill with HP AIV H5N1.

The origin of the 1918 pandemic is controversial. Taubenberger et al., (*Characterization of the* 1918 *influenza virus polymerase genes. Nature,* 2005, 437:889-893) suggested based on phylogenetics of the polymerase genes that the virus was entirely of avian origin. If the virus was of avian origin it might imply that the HP avian viruses circulating currently could cause a new pandemic by direct transmission to humans. However, there is consideration disagreement about the actual origin of the virus and many still believe that also this 1918 pandemic strain is a reassortant between a mammalian and avian virus most likely occurring from swine. Antigenic reassortment occurs when viral segments from two antigenic different viruses infect the same cell. The reassorted virus contains segments of both strains and if the newly introduced segment is HA (and NA) the complete antigenicity of the virus might change and the virus escapes the host immunity. The reassortant might be catastrophic if the virus is capable of efficient replication in the new host. In the worst case, such a reassorted strain might lead to a pandemic, world-spanning infection to which there is no pre-existing immunity in the human population. The pandemics of 1957 and 1968 were reassortants that acquired the HA, NA and PB1 and HA and PB1 genes from an aquatic source, respectively. In 1977, a strain identical to the H1N1 strains that circulated before 1957 re-emerged. Pigs are possible "mixing vessels" for reassorted viruses due to their receptor tropism for both a-(2,3) and a-(2,6) linkage to galactose. Other species like chicken and man might also serve as mixing vessels in the light of direct crossover to humans from an avian source after the discovery of a-(2,3) avian like receptor on cells also in humans and chickens.

The interpandemic evolution of influenza viruses has been thought to be caused by progressive antigenic drift due to the mutability of the RNA genome. H3N2 has been the predominant subtype circulating in humans since 1968 and has been in rapid drift as a single lineage while there has been slow replacement of antigenic variants of the H1N1 viruses. It has been shown that the rate of accumulating mutations is approximately $4\text{-}5\times10^{-3}$ substitutions per nucleotide per year for HA1; others predict a rate of $5.7\times10^{-3}$ substitutions per nucleotide per year. The HA and NA might evolve independently from each other and reassortments of the internal genes are also known. Positive selection has been inferred on codons involved at antibody antigenic sites, T-cell epitopes and sites important for virus egg growth properties. Recent research on viruses has suggested that the evolution of influenza does not always follow a constant rate, but is characterised by stochastic processes, short intervals of rapid evolution, and long intervals of neutral sequence evolution and slow extinction of coexisting virus lineages. The evolution seems also more influenced by reassortment events between co-circulating lineage and viral migration than previously believed.

Vaccination is the preferred choice for influenza prophylaxis. Inactivated influenza vaccines are licensed worldwide, while cold-adapted live vaccines are licensed only in Russia and the USA. The preferred prophylaxis of annual influenza infections is vaccination with inactivated protein vaccines from virus propagated in hens' eggs. Thus, the common vaccines are the inactivated vaccine viruses which are propagated in hens' eggs and inactivated by formaldehyde or β-propiolactone. There are three classes of inactivated vaccines; whole, split (chemically disrupted with ether or tributyl phosphate) and subunit (purified surface glycoproteins) administrated intramuscularly or subcutaneously. Whole inactivated influenza vaccine is not currently used due to high levels of side effects. The seasonal influenza vaccine (split and subunit) is trivalent, comprising H3N2 and H1N1 influenza A virus strains and an influenza B virus. The normal human vaccine dose is standardised to 15 μg HA protein of each virus component administered once in normal healthy adults and twice in children and other persons with no pre-existing influenza A immunity. The conventional vaccines induce merely a humoral immune response. The protective effect of the traditional protein split vaccine is very limited and because of the continuous evolution of influenza A virus strains and the type specific antibodies induced by the conventional vaccines, a new vaccine has to be produced every year based on the most recent circulating influenza A strain. Several vaccine improvements are necessary in case of a new emerging human strain. Egg production is too slow (6-12 months) in the case of emerging strains. If this strain is also an AIV virus highly pathogenic (HP) for poultry, egg production might be impossible because the virus kills the egg embryo. Also the availability of eggs might be limited and slow down vaccine production. In the case of no pre-existing immunity in the population, two vaccinations would be necessary, thereby further delaying the vaccine production. Even if there are no new pandemic influenza A among humans but only spread of a HPV AIV among poultry, a shortage of eggs will limit production of traditional seasonal influenza vaccines on eggs. In addition, traditional influenza protein vaccines do not have optimal protection as prophylaxis and no therapeutic effect. Thus, there is a need for new alternative influenza vaccines.

Although DNA vaccines were developed more than 16 years ago, clinical trials proceeding to stage I and II in humans are rare. Two veterinary DNA vaccines however, have been licensed; one for West Nile Virus (in horse) and a second for Infectious Hematopoietic Necrosis virus in Salmon. This demonstrates that DNA vaccines can have good protective effects and that new DNA vaccines are not limited by the size of the animal or species. The great success with DNA vaccines observed for the murine model for first generation DNA vaccines did not translate well to humans; nonetheless, researchers have recently demonstrated protective antibodies levels by a single dose of gene gun administrated HA DNA vaccine to humans.

"Nucleic acid immunization" or the commonly preferred name "DNA vaccines" are the inoculation of antigen encoding DNA or RNA as expression cassettes or expression vectors or which may be incorporated into viral vectors with the purpose of inducing immunity to the gene product. Thus, as used herein, DNA vaccines refer to all kinds of delivery systems for the antigen encoding naked DNA or RNA but exclude viral vector-based delivery. The vaccine gene can be in form of circular plasmid or a linear expression cassette with just the key features necessary for expression (promoter, the vaccine gene and polyadenylation signal). Delivery systems may most often be naked DNA in buffer with or without adjuvant, DNA coupled to nanoparticles and/or formulated into adjuvant containing compounds or inserted into live viral or bacterial vectors, such as adenovirus, adeno-associated virus, alphavirus, poxviruses, herpes virus etc. DNA vaccines hold great promise since they evoke both humoral and cell-mediated immunity, without the same dangers associated with live virus vaccines. In contrast to live attenuated virus vaccines DNA vaccines may be delivered to same or different tissue or cells than the live virus that has to bind to specific receptors. The production of antigens in their native forms improves the presentation of the antigens to the host immune system. Unlike live attenuated vaccines, DNA vaccines are not infectious and can not revert to virulence.

WO2006063101 describes a pandemic avian influenza vaccine based on an adenovirus vehicle with HA DNA isolated from the avian H5N1 influenza virus isolated during the outbreak in 2003-2005. The vaccine was tested in animals challenged with the same H5N1 influenza virus strain.

DNA vaccines induce an immune response which may be comparable to the response acquired by natural virus infection by activating both humoral and cell-mediated immunity (6,30). The broad response to DNA vaccines is a result of the encoded genes being expressed by the transfected host cell, inducing both a Th1 and Th2 immune responses. The production of antigens in their native form improves the presentation of the antigens to the host immune system. In contrast, the conventional inactivated influenza protein based vaccines only induce a humoral response (Th2), directed against the influenza surface glycoproteins. This type of response is ineffective against drifted virus variants and therefore the virus composition of the seasonal influenza vaccine has to be assessed every season. Antigenic cross-reactive responses are mainly induced by the more conserved influenza proteins like the nucleoprotein (NP) and the matrix (M) protein. By including these genes in a DNA vaccine higher cross reactivity between drifted and heterologous strains have been shown (4,7,8,13). However, cellular immunity alone cannot protect against infection since this requires antibodies.

Influenza infection and symptoms in ferrets are highly comparable to what is observed in humans. Therefore ferrets are one of the best models for influenza vaccination trials (22). Influenza HA DNA vaccines in ferrets has also previously proved effective (18,32).

It has previously been shown that H1N1 whole inactivated virus vaccine induced partly protection against infection with 1918 in mice (28). Also, recently, a DNA vaccine encoding the HA from 1918 showed complete protection of mice against a 1918 H1N1 challenge (16).

Influenza vaccines that have the ability to induce immune responses able to cross-react with drifted virus variants and even heterologous strains would be of great advantage for both annual vaccine development and in cases of emerging new strains.

SUMMARY OF THE INVENTION

The present invention provides regimens and compositions containing the hemagglutinin (HA) from pandemic influenza A, e.g. the 1918 H1N1 and/or the 1957 H2N2 and/or the 1968 H3N2 influenza A virus, useful as a therapeutic or prophylactic vaccine component against present day and future influenza A strains. The invention may optionally provide naked DNA and/or RNA molecules encoding the Neuraminidase (NA), matrix protein (M) and/or the nucleoprotein (NP) from pandemic influenza virus. The invention also concerns vaccines comprising naked DNA and/or RNA coding HA and/or NA from the new circulating 2001 H5N7 low pathogenic (LP) Avian influenza virus (AIV) strain (A/Mallard/Denmark/64650/03(H5N7)), the newly introduced and circulating March 2006 Denmark H5N1 high pathogenic Avian influenza A virus (AIV) strains A/buzzard/Denmark/6370/06 (H5N1), A/duck/Denmark/53-147-8/08 (H7N1) and A/widegeon/Denmark/66174/G18/04 (H2N3).

The data herein demonstrates that gene gun administrated codon optimised DNA vaccine in plasmid encoding HA and NA with or without M and NP based on the H1N1 pandemic virus from 1918 induced protection in ferrets against infection with a H1N1 (A/New Caledonia/20/99(H1N1)) present day virus. The circulating H1N1 strain in Europe in the 2006-2007 seasons is New Caledonia-like. The viruses are separated by a time interval of 89 years and differ by 21.2% in the HA1 protein. By comparison, a similar DNA vaccine encoding the HA and NA of (A/New Caledonia/20/99 (H1N1)) induced less protection. These results suggest not only a unique ability of the DNA vaccines but also a unique and unexpected feature of the 1918 HA and/or NA in inducing especially broad and efficient protective immunity against even extremely drifted strain variants.

The present invention discloses that an induced immune response with a DNA vaccine encoding HA and/or NA of the 1918 H1N1 influenza A gives a high level of cross protection against present day influenza infection. Tests were carried out in ferrets vaccinated with this DNA vaccine synthesised using human preferred codons of the 1918 H1N1 influenza and challenged with a contemporary H1N1 virus.

The results surprisingly show that the 1918 H1N1 DNA vaccines are as good as or better candidates for influenza prophylaxis than annual conventional protein based vaccines which frequently need to be updated to match the circulating influenza virus. DNA vaccination induces broader cross-reactivity against drifted strain and longer memory responses. It has been shown that a similar DNA vaccine may protect against the 1918 H1N1 recombinant strain (16). However, the results herein then suggest that the synthetic DNA vaccine based on the 1918 H1N1 sequences protects against extreme drifted variants represented by recent contemporary or seasonal circulating H1N1 strains. Thus it is likely that the suggested 1918 H1N1 DNA vaccine protects against H1N1 strains circulating for up to 89 years and therefore likely also future H1N1 variants. This is highly unexpected since traditional protein split vaccines only protects against the strain it is designed from and thus has to be produced from the actual circulating H1N1 strains sometimes as frequent as every year. Thus, a DNA vaccine encoding the HA and NA of 1918 H1N1 was not expected to protect against such a divergent strain as the present day H1N1, but it does.

Other aspects and advantages of the invention will be readily apparent from the following detailed description of the invention.

BRIEF DESCRIPTION OF THE DRAWINGS

FIG. 2A shows fever at day 2 post challenge.

FIG. 2B shows body weight loss by day 4 post challenge.

FIG. 2C shows virus titer in nasal washings at day 7 post challenge.

FIG. 2D shows clinical score for illness based on a scoring table for sneezing, nasal discharge and activity level.

DETAILED DESCRIPTION OF THE INVENTION

Figure 1A:
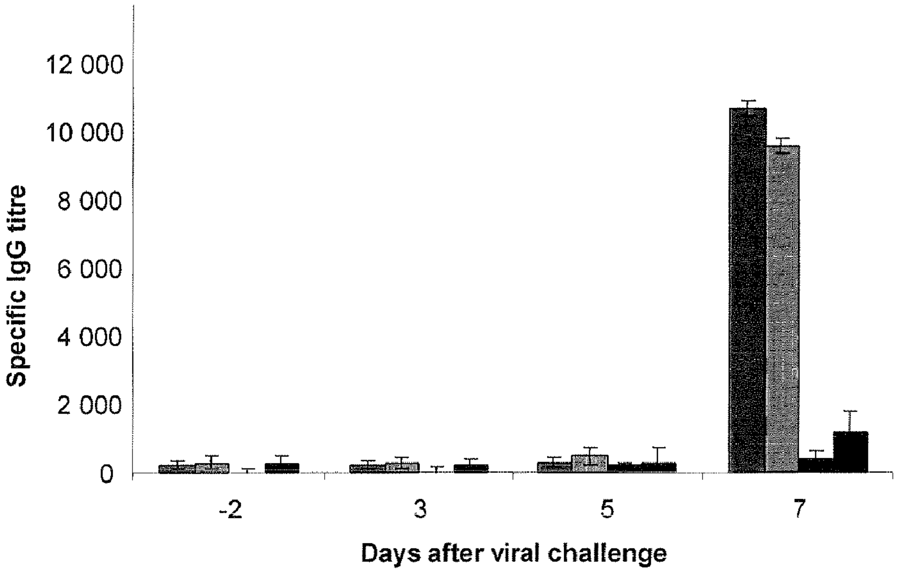
FIG. 1A illustrates the mean serum specific IgG antibody response (ELISA) to influenza A of A/New Caledonia/20/99 (H1N1) days after viral challenge. Six ferrets were in each group.

The present invention discloses the use of the naked DNA and/or RNA molecule encoding hemagglutinin (HA) from pandemic influenza, e.g. the 1918 H1N1 and/or the 1957 H2N2 and/or the 1968 H3N2 influenza A virus, as a vaccine component against present day and coming H1, H2, H3 containing influenza A infections in humans and/or swine. The naked DNA and/or RNA molecule encoding neuraminidase (NA) and/or matrix protein (M) and/or the nucleoprotein (NP) from pandemic influenza virus.

The naked DNA and/or RNA molecule encoding neuraminidase (NA) and/or matrix protein (M) and/or the nucleoprotein (NP) from pandemic influenza virus can optionally be included as vaccine components against present day and coming H1, H2, H3, N1, N2 containing influenza A infections in humans and/or swine.

The vaccine of the invention is believed to offer many of the advantages a DNA vaccine can provide over conventional vaccines. More particularly, it may be produced in high amounts in short time, abolishing the need for propagation in eggs; it is cost-effective, reproducible and the final product does not require cold storage conditions, because DNA is stable and resistant to the extremes of temperature. All currently licensed inactivated vaccines are efficient at inducing humoral antibody responses but only live attenuated virus vaccines efficiently induce a cytotoxic cellular response as well. However, DNA vaccines have the ability to induce a cytotoxic cellular response as well as a humoral antibody response. Therefore, these vaccines may better mimic the natural response to viral infection than inactivated vaccines in respect to specificity and antibodies isotypes.

The components in the vaccine are naked DNA and/or RNA coding for the hemagglutinin and/or the neuraminidase and/or matrix protein (M) and/or the nucleoprotein (NP) from pandemic influenza strains, preferably with a mixture of such proteins from several pandemic strains.

In a preferred embodiment of the invention the DNA and/or RNA codons are humanized e.g. the DNA sequence for hemagglutinin and neuraminidase and Matrix and Nucleoprotein is changed so the sequence coding for said proteins is changed to be optimally expressed in mammalian cells.

The invention also discloses the vaccines against present day human and swine influenza A infection comprising the above-mentioned naked DNA and/or RNA coding hemagglutinin and/or neuraminidase and/or a matrix protein and/or the hemagglutinin protein and/or DNA or RNA from the pandemic influenza, e.g., the 1918 H1N1 and/or the 1957 H2N2 and/or the 1968 H3N2 influenza A virus, preferably with a mixture from various influenza strains.

In another embodiment the vaccine comprises naked DNA and/or RNA coding HA and/or NA from 1918 H1N1 strain plus HA and NA from 1957 H2N2 plus HA from 1968 H3N2 virus strains as DNA vaccines and/or proteins. The vaccine is intended to protect humans against circulating H1, H2, and H3 influenza A strains.

In another embodiment the vaccine comprises naked DNA and/or RNA molecules encoding HA and/or NA from the new circulating 2001 H5N7 low pathogenic (LP) Avian influenza virus (AIV) strain (A/Mallard/Denmark/64650/03(H5N7)) as DNA vaccines and/or proteins. The vaccine is intended to protect birds and humans and swine against H5, H7 and/or H2 containing influenza A strains.

In another embodiment the vaccine comprises naked DNA and/or RNA molecules encoding HA with or without NA and/or M and/or NP from the newly introduced and circulating March 2006 Denmark H5N1 high pathogenic Avian influenza A virus (MV) strain (A/buzzard/Denmark/6370/06 (H5N1)), A/duck/Denmark/53-147-8/08 (H7N1) and A/widegeon/Denmark/66174/G18/04 (H2N3). The vaccine is intended to broadly protect birds and humans and swine against any H5 containing influenza A strains.

Above mentioned vaccines can be used both prophylactically and therapeutically.

Definitions

Hemagglutinin

The name hemagglutinin is derived from the viruses' ability to agglutinate red blood cells. The envelope glycoprotein HA is a rod-like shaped trimer of identical monomers. The HA protein is synthesised in the infected cell as a single polypeptide chain, HA0. This initial molecule has to be cleaved by the host cell proteases into disulfide linked HA1 (47 kDa) and HA2 (29 kDa) subunits in order for the virus to mediate membrane fusion and subsequent infection. The HA1 subunit is the globular domain of the HA molecule which comprises the receptor binding site, responsible for virus attachment to sialic acid receptors on the host cell. The five antigenic sites A, B, C, D and E at the globular head direct the host antibody response. The HA is the primary viral antigen and the only antigen inducing a virus neutralising response in the host. The HA main functions are virion-to-host cell membrane fusion and fusion of the endocytosed virion with the endosomal membrane allowing release of the genome into the cytoplasm. HA is a prototype 1 integral membrane protein that is targeted to the ER membrane through an N-terminal signal peptide sequence and cleaved by signal peptidase. The HA2 subunit forms the stem of the molecule. The N-terminus of HA2 (fusion peptide) is hydrophobic and is highly conserved in the HAs of different influenza virus strains, and it is essential in HA fusion activity. The HA is post translationally modified by addition of N-linked carbohydrates at asparagine residues (N) on each monomer and palmitic acid to cysteine (C) residues in the cytoplasmic tail region. HA binds to 5-N-acetyl neuramic acid (sialic acid) on the host cell surface and positions and are essential in determining preferred host cell tropism. Human infectious strains preferentially bind to sialic acid with a-(2,6) linkage to galactose, while avian influenza viruses (AIV) preferentially bind to a-(2,3), Neuraminidase:

The neuraminidase (NA) is a class II membrane envelope glycoprotein with enzymatic activity. It is a tetramer of identical monomers forming a mushroom-like shape. The hydrophobic stalk region is membrane anchored and the globular head contains the enzyme active site and the three antigenic sites A, B and C of the molecule. The main function of the NA is to catalyse the cleavage of glycosidic linkages adjacent to sialic acid. The activity is essential for the progeny virion for efficient release from the surface of the infected cell. Like HA, NA is posttranslational modified with N-linked glycosylations. The NA molecule is target for antiviral drugs like zanamivir [5-acetamido-4-guanidino-6-(1,2,3-trihydroxypropyl)-5,6-dihydro-4H-pyran-2-carboxylic acid] and oseltamivir [(3R,4R,5S)-4-acetylamino-5-amino-3-(1-ethylpropoxy)-1-cyclohexene-1-carboxylic acid ethyl ester]. Inhibition of NA prevents virus release from the infected cell and delays virus propagation. Currently nine subtypes of NA have been recognised.

Matrix Proteins:

The matrix proteins consist of two proteins, the ion channel protein M2 and the structural protein M1. The M1 protein is a matrix protein lining the interior side of the membrane derived from the infected host cell giving structure and rigidity to the membrane. The M1 protein contains a hydrophobic lipid binding domain and a RNP binding domain. Assembly of negative stranded RNA viruses requires localisation of M1 proteins to the plasma membrane. The M1 protein binds to the cytoplasmic tails of HA, NA and M2. NA stimulates the membrane binding by the M1 proteins. M1 together with NS2 is required for export of genomic RNPs from the nucleus, M1 also inhibits RNA synthesis. The M2 protein is a small homotetramer integral membrane protein, and ion channel, translated from a spliced mRNA in +1 reading frame. The ion channel is activated by the low pH of the endosome, allowing protons to enter the interior of the virus leading to conformational changes in M1 and disrupting the M1-RNP interactions. The M2 ion channel is a target for antiviral drugs like amantadine and rimantadine.

Nucleoprotein:

The Nucleoprotein (NP) is highly basic and binds the sugar-phosphate backbone of viral RNA in a non-sequence specific manner approximately every 25 nucleotides. NP interacts with both PB1 and PB2 and with a variety of other viral and cellular proteins. The interaction with M1 controls the transcriptional activity of RNPs and their intracellular trafficking. NP is mainly responsible for maintaining the structure of RNPs and in regulation of genome transcription and replication, the polymerase can not use naked viral RNA as template. NP associated with viral RNA is abundant in extracellular fluid and lung tissue during severe influenza A infection.

The 1918 Influenza Virus:

The most severe pandemic this century has been the 1918 H1N1 "Spanish flu". The virus killed between 40 and 50 million people worldwide during 1918 and 1919 (10). Based on preserved specimens, all genes have been genetically characterised and the entire virus has now been restored (27). This gives a unique opportunity to elucidate the mechanisms of immunopathogenesis of the pandemic strain.

The pandemic strains of 1957 (H2N2) and 1968 (H3N2) were both a result of genetic reassortment with avian viruses (11,17). The origin of the 1918 pandemic is debated. Taubenberger et at., (26) suggested based on phylogenetic analysis of the polymerase genes that the virus was entirely of avian origin. However, there are large disagreements about the actual origin of the virus and many still believe that this pandemic strain also was a reassortant between a mammalian and avian virus (1,26). The hemagglutinin (HA) and neuraminidase (NA) genes of the 1918 H1N1 strain did not possess known genetic indicators for high virulence that could have explained the severity observed in humans (19, 20). However, the HA (and NA) protein on a backbone of recent human viruses conferred enhanced pathogenicity in mice (12,29). It might have been the combination of genes more than the HA itself that caused the lethal phenotype (27). The uncertainty about the origin and the mechanisms of high virulence of the 1918 H1N1 virus has raised questions if it is possible to develop protective immunity to this virus. Recently it has been published that a DNA vaccine encoding the HA of the 1918 H1N1 strain showed protection to a lethal challenge of the recombinant 1918 H1N1 virus strain in mice (Kong W, Hood C, Yang Z, Wei C, Xu L, Garcia-Sastre A, Tumpey T M, Nabel G J. Protective immunity to lethal challenge of the 1918 pandemic influenza virus by vaccination. PNAS 103(43):15987-91 (2006)).

DNA Vaccines:

DNA vaccines are here defined as naked DNA or RNA, DNA or RNA in solution for direct intramuscular or subcutaneous injection with or without electroporation or coupled to particles, e.g., gold beads for gene gun administration. The DNA can be linear containing only a promoter, the influenza genes and polyadenylation signal or this expression cassette in an expression plasmid.

The administration of DNA vaccine can be by saline or buffered saline injection of naked DNA or RNA, or injection of DNA plasmid or linear gene expressing DNA fragments coupled to particles, or inoculated by gene gun.

The two most common types of DNA vaccine administration are saline injection of naked DNA and gene gun DNA inoculations (DNA coated on solid gold beads administrated with helium pressure). Saline intra muscular injections of DNA preferentially generate a Th1 IgG2a response while gene gun delivery tends to initiate a more Th2 IgG1 response. Intramuscular injected plasmids are at risk of being degraded by extracellular deoxyribonucleases, however, the responses induced are often more long-lived than those induced by the gene gun method. Vaccination by gene gun delivery of DNA to the epidermis has proven to be the most effective method of immunization, probably because the skin contains all the necessary cells types, including professional antigen presenting cells (APC), for eliciting both humoral and cytotoxic cellular immune responses (Langerhans and dendritic cells). Complete protection from a lethal dose of influenza virus has been obtained with as little as 1 μg DNA in mice. The standard DNA vaccine consists of a vector with a gene of interest cloned into a bacterial plasmid engineered for optimal expression in eukaryotic cells. In one embodiment, a vaccine vector includes an origin of replication allowing for production in bacteria, a bacterial antibiotic resistance gene allowing for plasmid selection in bacterial culture, a strong constitutive promoter for optimal expression in mammalian cells (eukaryotic promoters such as those derived from cytomegalovirus (CMV) or simian virus provide the highest gene expression), a polyadenylation sequence to stabilise the mRNA transcripts, such as bovine growth hormone (BHG) or simian virus polyadenylation, and a multiple cloning site for insertion of an antigen gene. An intron A sequence can be included to improve expression of genes. Many bacterial DNA vaccine vectors contain unmethylated cytidinephosphate-guanosine (CpG) dinucleotide motifs that may elicit strong innate immune responses in the host.

In one embodiment, a eukaryotic expression vector contains a constitutive eukaryotic promoter, an intron, a polylinker which allows for convenient insertion of a vaccine gene, and a polyadenylation signal is used. Suitable expression vectors are known the art and may be used as backbones engineered to contain the elements described herein. For example, commercially available vectors (e.g., the WRG7079 vector available form PowderJect Vaccines, Madison, WI) and/or vectors described in the literature (e.g., Corbet et al, 2000 (5)) can be used as a backbone to contain the elements described herein. For example, in one embodiment, an expression vector of the invention is designed to contain one or more of the secretory signal from an influenza virus (e.g., the influenza A 1918 HA or NA secretory signals).

In recent years there have been several approaches to enhance and customise the immune response to DNA vaccine constructs (2nd generation DNA vaccines). For instance dicistronic vectors or multiple gene expressing plasmids have been used to express two genes simultaneously. Specific promoters have been engineered that restrict gene expression to certain tissues, and cytokine/antigen fusion genes have been constructed to enhance the immune response. Furthermore, genes may be codon optimised for optimal gene expression in the host and naïve leader sequences may be substituted with optimised leaders increasing translation efficiency.

Viral DNA Vaccines:

DNA can be delivered by a viral vector such as Adenovirus, Modified vaccinia virus Ankara (MVA), Vaccinia, Adeno-associated virus (AAV), Alphavirus etc. Viral DNA vaccines are not a part of the present study and are not encompassed by this invention.

Codon Optimization:

Codon optimization is the complete exchange of the virus codons to those of highly expressed human genes and therefore also mammalian genes that include swine. Codon optimization does not change the encoded amino acids of the protein antigens encoded but may increase the eukaryotic protein expression in mammalian cells. Since genes of highly expressed human proteins has a high content of C and G there are an increased possibility of generating both immune stimulatory GpG motifs but also immune inhibitory GC sequences. Genes engineered using codon optimization are called "humanized" genes and are frequently used in DNA vaccines to enhance expression.

The DNA or RNA sequence for hemagglutinin and neuraminidase and Matrix and Nucleoprotein is changed so the sequence coding for said proteins is changed to be optimally expressed in humans.

In one embodiment, the invention provides the use of the 1918 HA and/or NA codon-optimized genes in a DNA vaccine against all seasonal circulating H1N1 influenza A strains including the A/New Caledonia/20/99(H1N1) like virus.

TABLE 1

| nucleotide and amino acid sequences of the codon optimized genes and the proteins they express. |
|---|
| HA 1918 synthetic gene 0607838, Based on acc. No.: AF117241: A/South Carolina/1/18<br>SEQ ID NO: 1: Nucleotide |
| ATGGAGGCCAGGCTGCTGGTGCTGCTGTGCGCCTTCGCCGCCACCAACGC<br>CGACACCATCTGCATCGGCTACCACGCCAACAACAGCACCGACACCGTGG<br>ATACCGTGCTGGAGAAGAACGTGACCGTGACCCACAGCGTGAACCTGCTG<br>GAGGACAGCCACAACGGCAAGCTGTGCAAGCTGAAGGGAATCGCTCCCCT<br>GCAGCTGGGCAAGTGCAACATCGCCGGCTGGCTGCTGGGCAACCCCGAGT<br>GCGACCTGCTGCTGACCGCCAGCAGCTGGTCCTACATCGTGGAGACCAGC<br>AACAGCGAGAACGGCACCTGCTACCCCGGCGACTTCATCGACTACGAGGA<br>GCTGCGGGAGCAGCTGTCCAGCGTGAGCAGCTTCGAGAAGTTCGAGATCT<br>TCCCCAAGACCAGCTCCTGGCCCAACCACGAGACCACCAAGGGCGTGACC<br>GCCGCCTGTAGCTACGCCGGAGCCAGCAGCTTCTACAGAAACCTGCTGTG<br>GCTGACCAAGAAGGGCAGCAGCTACCCCAAGCTGTCCAAGAGCTACGTGA<br>ACAACAAGGGCAAGGAAGTGCTGGTGCTGTGGGGCGTGCACCACCCCCCT<br>ACCGGCACCGACCAGCAGAGCCTGTACCAGAACGCCGACGCCTACGTGAG<br>CGTGGGCAGCAGCAAGTACAACAGAAGGTTCACCCCCGAGATCGCCGCCA<br>GGCCCAAGGTGCGCGACCAGGCCGGCAGGATGAACTACTACTGGACCCTG<br>CTGGAGCCCGGCGACACCATCACCTTCGAGGCCACCGGCAACCTGATCGC<br>CCCTTGGTACGCTTCGCCCTGAACAGGGGCAGGGGCAGCGGCATCATCAC<br>CAGCGACGCCCCCGTGCACGACTGCAACACCAAGTGCCAGACCCCCCACG |

TABLE 1-continued

| nucleotide and amino acid sequences of the codon optimized genes and the proteins they express. |
|---|
| GAGCCATCAACAGCAGCCTGCCCTTCCAGAACATCCACCCCGTGACCATC<br>GGCGAGTGCCCCAAGTACGTGAGAAGCACCAAGCTGAGGATGGCCACCGG<br>CCTGAGGAACATCCCCAGCATCCAGAGCAGGGGCCTGTTCGGAGCCATCG<br>CCGGATTCATCGAGGGCGGCTGGACCGGCATGATCGACGGCTGGTACGGC<br>TACCACCACCAGAACGAGCAGGGCAGCGGCTACGCCGCCGACCAGAAGAG<br>CACCCAGAACGCCATCGACGGCATCACCAACAAGGTGAACAGCGTGATCG<br>AGAAGATGAACACCCAGTTCACCGCCGTGGGCAAGGAGTTCAACAACCTG<br>CAGAGGCGGATCGAGAACCTGAACAAGAAGGTGGACGACGGCTTCCTGGA<br>CATCTGGACCTACAACGCCGAGCTGCTGGTGCTGCTGGAGAACGAGAGGA<br>CCCTGGACTTCCACGACAGCAACGTGAGGAACCTGTACGAGAAGGTGAAG<br>AGCCAGCTGAAGAACAACGCCAAGGAGATCGGCAACGGCTGCTTCGAGTT<br>CTACCACAAGTGCGACGACGCCTGCATGGAGAGCGTGAGAAACGGCACCT<br>ACGACTACCCCAAGTACAGCGAGGAGAGCAAGCTGAACCGGGAGGAGATC<br>GACGGCGTGAAGCTGGAGAGCATGCGCGTGTACCAGATCCTGGCCATCTA<br>CAGCACCGTGGCCAGCAGCCTGGTGCTGCTGGTGTCCCTGGGAGCCATCA<br>GCTTTTGGATGTGCAGCAACGGCAGCCTGCAGTGCAGGATCTGCATCTGA |
| SEQ ID NO: 2 Amino acid |
| MEARLLVLLCAFAATNADTICIGYHANNSTDTVDTVLEKNVTVTHSVNLL<br>EDSHNGKLCKLKGIAPLQLGKCNIAGWLLGNPECDLLLTASSWSYIVETS<br>NSENGTCYPGDFIDYEELREQLSSVSSFEKFEIFPKTSSWPNHETTKGVT<br>AACSYAGASSFYRNLLWLTKKGSSYPKLSKSYVNNKGKEVLVLWGVHHPP<br>TGTDQQSLYQNADAYVSVGSSKYNRRFTPEIAARPKVRDQAGRMNYYWTL<br>LEPGDTITFEATGNLIAPWYAFALNRGSGSGIITSDAPVHDCNTKCQTPH<br>GAINSSLPFQNIHPVTIGECPKYVRSTKLRMATGLRNIPSIQSRGLFGAI<br>AGFIEGGWTGMIDGWYGYHHQNEQGSGYAADQKSTQNAIDGITNKVNSVI<br>EKMNTQFTAVGKEFNNLERRIENLNKKVDDGFLDIWTYNAELLVLLENER<br>TLDFHDSNVRNLYEKVKSQLKNNAKEIGNGCFEFYHKCDDACMESVRNGT<br>YDYPKYSEESKLNREEIDGVKLESMGVYQILAIYSTVASSLVLLVSLGAI<br>SFWMCSNGSLQCRICI. |
| NA 1918 synthetic gene 0607869, Based on acc. No.: AF250356: A/Brevig mission/1/1918<br>SEQ ID NO: 3 Nucleotide |
| ATGAACCCCAACCAGAAGATCATCACCATCGGCAGCATCTGCATGGTGGT<br>GGGCATCATCAGCCTGATCCTGCAGATCGGCAACATCATCAGCATCTGGG<br>TGTCCCACAGCATCCAGACCGGCAACCAGAACCACCCCGAGACCTGCAAC<br>CAGTCCATCATCACCTACGAGAACAACACCTGGGTGAACCAGACCTACGT<br>GAACATCAGCAACACCAACGTGGTGGCCGGCCAGGACGCCACCTCCGTGA<br>TCCTGACAGGCAACAGCAGCCTGTGCCCCATCAGCGGCTGGGCCATCTAC<br>AGCAAGGACAACGGCATCAGGATCGGCAGCAAGGGCGACGTGTTCGTGAT<br>CAGAGAGCCCTTCATCAGCTGCAGCCACCTGGAATGCAGGACCTTCTTCC<br>TGACCCAAGGAGCCCTGCTGAACGACAAGCACAGCAACGGCACCGTGAAG<br>GACAGAAGCCCCTACAGGACCCTGATGAGCTGCCCCGTGGGCGAGGCTCC<br>CAGCCCCTACAACAGCAGATTCGAGAGCGTGGCCTGCTCCGCCAGCGCCT<br>GCCACGACGGCATGGGCTGGCTGACCATCGGCATCAGCGGCCCTGACAAC<br>GGGGCCGTGGCCGTGCTGAAGTACAACGGAATCATCACCGACACCATCAA<br>GAGCTGGCGGAACAACATCCTGAGGACCCAGGAAAGCGAGTGCGCCTGCG<br>TGAACGGCAGCTGCTTCACCATCATGACCGACGGCCCCAGCAACGGCCAG<br>GCCAGCTACAAGATCCTGAAGATCGAGAAGGGCAAGGTGACCAAGAGCAT<br>CGAGCTGAACGCCCCCAACTACCACTACGAGGAATGCAGCTGCTACCCCG<br>ACACCGGCAAGGTCATGTGCGTGTGCAGGGACAACTGGCACGGCAGCAAC<br>AGGCCCTGGGTGTCCTTCGACCAGAACCTGGACTACCAGATCGGATACAT<br>CTGCAGCGGCGTGTTCGGCGACAACCCCAGGCCCAACGACGGCACCGGCA<br>GCTGCGGCCCTGTGAGCAGCAACGGGGCCAATGGCATCAAGGGCTTCAGC<br>TTCAGATACGACAACGGCGTGTGGATCGGCCGCACCAAGAGCACCAGCAG<br>CAGATCCGGCTTCGAGATGATCTGGGACCCCAACGGCTGGACCGAGACCG<br>ACAGCAGCTTCAGCGTGAGGCAGGACATCGTGGCCATCACCGACTGGTCC<br>GGCTACAGCGGCAGCTTCGTGCAGCACCCCGAGCTGACCGGCCTGGACTG<br>CATGAGGCCCTGTTTCTGGGTGGAGCTGATCAGAGGCCAGCCCAAGGAGA<br>ACACCATCTGGACCAGCGGCAGCAGCATCAGCTTTTGCGGCGTGAACAGC<br>GACACCGTGGGCTGGTCCTGGCCCGACGGGGCCGAGCTGCCCTTCAGCAT<br>CGATAAGTGA |
| SEQ ID NO: 4: Amino acid |
| MNPNQKIITIGSICMVVGIISLILQIGNIISIWVSHSIQTGNQNHPETCN<br>QSIITYENNTWVNQTYVNISNTNVVAGQDATSVILTGNSSLCPISGWAIY<br>SKDNGIRIGSKGDVFVIREPFISCSHLECRTFFLTQGALLNDKHSNGTVK<br>DRSPYRTLMSCPVGEAPSPYNSRFESVAWSASACHDGMGWLTIGISGPDN<br>GAVAVLKYNGIITDTIKSWRNNILRTQFSECACVNGSCFTIMTDGPSNGQ |

TABLE 1-continued nucleotide and amino acid sequences of the codon optimized genes and the proteins they express.

ASYKILKIEKGKVTKSIELNAPNYHYEECSCYPDTGKVMCVCRDNWHGSN
RPWVSFDQNLDYQIGYICSGVFGDNPRPNDGTGSCGPVSSNGANGIKGFS
FRYDNGVWIGRTKSTSSRSGFEMIWDPNGWTETDSSFSVRQDIVAITDWS
GYSGSFVQHPELTGLDCMRPCFWVELIRGQPKENTIWTSGSSISFCGVNS
DTVGWSWPDGAELPFSIDK.

NP 1918 synthetic gene 0607866, Based on acc. No.: AY44935: A/Brevig mission/1/1918
SEQ ID NO: 5: Nucleotide ATGGCCAGCCAGGGCACCAAGAGAAGCTACGAGCAGATGGAAACCGACGG
CGAGAGGCAGAACGCCACCGAGATCAGGGCCAGCGTGGGCAGGATGATCG
GCGGCATCGGCAGGTTCTACATCCAGATGTGCACCGAGCTGAAGCTGTCC
GACTACGAGGGCAGGCTGATCCAGAACAGCATCACCATCGAGAGGATGGT
GCTGTCCGCCTTCGACGAGAGAAGAAACAAGTACCTGGAAGAGCACCCCA
GCGCCGGCAAGGACCCCAAGAAAACCGGCGGACCCATCTACAGAAGGATC
GACGGCAAGTGGATGAGAGAGCTGATCCTGTACGACAAGGAGGAAATCAG
AAGGATCTGGCGGCAGGCCAACAACGGCGAGGACGCCACAGCCGGCCTGA
CCCACATGATGATCTGGCACAGCAACCTGAACGACGCCACCTACCAGAGG
ACCAGGGCCCTCGTCAGAACCGGCATGGACCCCCGGATGTGCAGCCTGAT
GCAGGGCAGCACACTGCCCAGAAGAAGCGGAGCTGCTGGAGCCGCCGTGA
AGGGCGTGGGCACCATGGTGATGGAACTGATCAGGATGATCAAGAGGGGC
ATCAACGACAGGAACTTTTGGAGGGGCGAGAACGGCAGAAGGACCAGGAT
CGCCTACGAGAGGATGTGCAACATCCTGAAGGGCAAGTTCCAGACAGCCG
CCCAGAGGGCCATGATGGACCAGGTCCGGGAGAGCAGGAACCCCGGCAAC
GCCGAGATCGAGGACCTGATCTTCCTGGCCAGAAGCGCCCTGATCCTGAG
GGGCAGCGTGGCCCACAAGAGCTGCCTGCCCGCCTGCGTGTACGGACCCG
CCGTGGCCAGCGGCTACGACTTCGAGAGAGAGGGCTACAGCCTGGTCGGC
ATCGACCCCTTCAGGCTGCTGCAGAACTCCCAGGTGTACTCTCTGATCAG
GCCCAACGAGAACCCCGCCCACAAGTCCCAGCTGGTCTGGATGGCCTGCC
ACAGCGCCGCCTTCGAGGATCTGAGAGTGAGCAGCTTCATCAGGGGCACC
AGAGTGGTGCCCAGGGGCAAGCTGTCCACCAGGGGCGTGCAGATCGCCAG
CAACGAGAACATGGAAACCATGGACAGCAGCACCCTGGAACTGAGAAGCA
GGTACTGGGCCATCAGGACCAGAAGCGGCGGCAACACCAACCAGCAGAGG
GCCAGCGCCGGACAGATCAGCGTGCAGCCCACCTTCTCCGTGCAGAGGAA
CCTGCCCTTCGAGAGGGCCACCATCATGGCCGCCTTCACCGGCAACACCG
AGGGCAGGACCAGCGACATGAGGACCGAGATCATCAGAATGATGGAAAGC
GCCAGGCCCGAGGACGTGAGCTTCCAGGGCAGGGGCGTGTTCGAGCTGTC
CGATGAGAAGGCCACCTCCCCCATCGTGCCCAGCTTCGACATGAGCAACG
AGGGCAGCTACTTCTTCGGCGACAACGCCGAGGAATACGACAACTGA SEQ ID NO: 6: Amino acid MASQGTKRSYEQMETDGERQNATEIRASVGRMIGGIGRFYIQMCTELKLS
DYEGRLIQNSITIERMVLSAFDERRNKYLEEHPSAGKDPKKTGGPIYRRI
DGKWMRELILYDKEEIRRIWRQANNGEDATAGLTHMMIWHSNLNDATYQR
TRALVRTGMDPRMCSLMQGSTLPRRSGAAGAAVKGVGTMVMELIRMIKRG
INDRNFWRGENGRRTRIAYERMCNILKGKFQTAAQRAMMDQVRESRNPGN
AEIEDLIFLARSALILRGSVAHKSCLPACVYGPAVASGYDFEREGYSLVG
IDPFRLLQNSQVYSLIRPNENPAHKSQLVWMACHSAAFEDLRVSSFIRGT
RVVPRGKLSTRGVQIASNENMETMDSSTLELRSRYWAIRTRSGGNTNQQR
ASAGQISVQPTFSVQRNLPFERATIMAAFTGNTEGRTSDMRTEIIRMMES
ARPEDVSFQGRGVFELSDEKATSPIVPSFDMSNEGSYFFGDNAEEYDN.

M 1918 synthetic gene 0607868, Based on acc. No.: AY130766: A/Brevig mission/1/1918
SEQ ID NO: 7: Nucleotide ATGAGTCTTTTAACCGAGGTCGAAACGTACGTTCTCTCTATCGTCCCGTC
AGGCCCCCTCAAAGCCGAGATCGCGCAGAGACTTGAAGATGTCTTTGCAG
GGAAGAACACCGATCTTGAGGCTCTCATGGAATGGCTAAAGACAAGACCA
ATCCTGTCACCTCTGACTAAGGGGATTTTAGGATTTGTGTTCACGCTCAC
CGTGCCCAGTGAGCGAGGACTGCAGCGTAGACGCTTTGTCCAAAATGCCC
TTAATGGGAACGGGGATCCAAATAACATGGACAGAGCAGTTAAACTGTAC
AGGAAGCTTAAGAGGGAGATAACATTCCATGGGGCCAAAGAAGTAGCACT
CAGTTATTCCGCTGGTGCACTTGCCAGTTGTATGGGCCTCATATACAACA
GGATGGGGACTGTGACCACTGAAGTGGCATTTGGCCTGGTATGCGCAACC
TGTGAACAGATTGCTGATTCCCAGCATCGGTCTCACAGGCAAATGGTGAC
AACAACCAATCCACTAATCAGACATGAGAACAGAATGGTACTGGCCAGCA
CTACGGCTAAGGCTATGGAGCAAATGGCTGGATCGAGTGAGCAAGCAGCA
GAGGCCATGGAGGTTGCTAGTCAGGCTAGGCAAATGGTGCAGGCGATGAG
AACCATTGGGACTCATCCTAGCTCCAGTGCTGGTCTGAAAGACGATCTTA
TTGAAAATTTGCAGGCCTACCAGAAACGAATGGGGGTGCAGATGCAACGA
TTCAAGTGATCCTCTCGTTATTGCCGCAAGTATCATTGGGATCTTGCACT
TGATATTGTGGATTCTTGATCGTCTTTTTTTCAAATGCATTTATCGTCGC
CTTAAATACGGTTTGAAAAGAGGGCCTTCTACGGAAGGAGTGCCGGAGTC
TATGAGGGAAGAATATCGAAAGGAACAGCAGAGTGCTGTGGATGTTGACG
ATGGTCATTTTGTCAACATAGAGCTGGAGTAAGGCGCC Amino acid
SEQ ID NO: 8: M1 protein MSLLTEVETYVLSIVPSGPLKAEIAQRLEDVFAGKNTDLEALMEWLKTRP
ILSPLTKGILGFVFTLTVPSERGLQRRRFVQNALNGNGDPNNMDRAVKLY
RKLKREITFHGAKEVALSYSAGALASCMGLIYNRMGTVTTEVAFGLVCAT
CEQIADSQHRSHRQMVTTTNPLIRHENRMVLASTTAKAMEQMAGSSEQAA
EAMEVASQARQMVQAMRTIGTHPSSSAGLKDDLIENLQAYQKRMGVQMQR
FK.

SEQ ID NO: 9: M2 protein

MSLLTEVETPTRNFWGCRCNDSSDPLVIAASIIGILHLILWILDRLFFKC
IYRRLKYGLKRGPSTEGVPESMREEYRKEQQSAVDVDDGHFVNIELE.

The 1918 HA and NA amino sequences are publicly available (GenBank A/south Carolina/1/18 AF117241, A/Brevig Mission/1/18 AF250356) and can be translated into DNA using standard optimal codons for eukaryotic mammalian expression using standard expression vectors (key features: CMV promoter, intron A, Kozak sequence, vaccine gene inclusive of its secretion sequence, stop codon, Polyadenylation A, kanamycin resistance gene) are included for growing and selection of transfected *E. coli* for plasmid DNA production.

DNA vaccination with the 1918 H1N1 HA and NA synthetic codon optimized genes using gene gun standard conditions induces protective immunity to present day circulating influenza A virus as exemplified using A/New Caledonia/20/99(H1N1) virus challenge in DNA vaccinated ferrets (Mustela Putorius Furo). This is highly surprising since the two viruses are separated by more than 80 years of antigenic drift and show about 21% difference in the HA1 protein. Normally a protective protein vaccine must be based upon the amino acid sequence of the circulating seasonal influenza A strain to induce protection. Moreover the protection by the 1918 DNA vaccine against 2007 circulating strain is more consistent than the traditional protein vaccine based on the homologous circulating strain (New Caledonia). This suggest that the 1918 based DNA vaccine induces a much broader protective immunity that protects against influenza A H1N1 strains from 1918 to present time and perhaps beyond.

The unusually broad protection may be due to a unique amino acid sequence in the 1918 HA and/or NA proteins inducing broader protective antibodies to special epitopes or cellular immunity or immune adjuvants effect, or a particular gene expression or particular immune induction by the optimized nucleotide sequence of the particular 1918 H1N1 genes, or some or all of these factors in combination.

The advantages are that a limited number of vaccine components delivered as a DNA vaccine either as naked DNA or RNA as plasmid or linear encoding sequences or incorporated into recombinant virus provide for more efficient delivery.

The discovery of a broad protection induced by the pandemic influenza A strain 1918 H1N1 may suggest that a similar good protection may be obtained against circulating H2 strains using DNA vaccines based on HA and/or NA from the 1958 H2N2 pandemic strain and against circulating H3 strains using DNA vaccines based in HA and/or NA from the 1968 pandemic strain.

The unusually broad and/or efficient protection obtained using a pandemic influenza A strain instead of the present day circulating strains may be due to special features in the sequence of the first new pathogenic and spreading virus. These features may gradually wane by accumulation of sequence changes during years of adaptation to the human and swine population.

If the protective feature is contained in the encoded amino acid sequence of the HA and/or NA 1918 and not the nucleotide sequence then the HA and/or NA protein(s) from 1918 may be used alone as an alternative to DNA or in combination with the DNA vaccine for immunization or vaccinations.

The use of the DNA vaccine components may serve as an adjuvant for the protein components and thus the protein and the DNA can be preferentially administered together as a mixed vaccine.

As a more universal DNA and/or protein vaccine against contemporary influenza in humans and/or swine a mixture may be used of HA and NA from the 1918 H1N1 pandemic strain plus HA and/or NA from the 1957 H2N2 pandemic strain plus HA from the 1968 H3N2 pandemic strain, where the N2 component is similar to the NA of the preferred earlier 1957 H2N2 strain.

TABLE 2 nucleotide and amino acid sequences of the codon optimized genes and the proteins they express (not codon optimized).

HA H3N2 Acc. No.: AB295605: A/Aichi/2/1968(H3N2)
SEQ ID NO: 10: Nucleotide

ATAATTCTATTAATCATGAAGACCATCATTGCTTTGAGCTACATTTTCTG
TCTGGCTCTCGGCCAAGACCTTCCAGGAAATGACAACAGCACAGCAACGC
TGTGCCTGGGACATCATGCGGTGCCAAACGGAACACTAGTGAAAACAATC
ACAGATGATCAGATTGAAGTGACTAATGCTACTGAGCTAGTTCAGAGCTC
CTCAACGGGGAAAATATGCAACAATCCTCATCGAATCCTTGATGGAATAG
ACTGCACACTGATAGATGCTCTATTGGGGGACCCTCATTGTGATGTTTTT
CAAAATGAGACATGGGACCTTTTCGTTGAACGCAGCAAAGCTTTCAGCAA
CTGTTACCCTTATGATGTGCCAGATTATGCCTCCCTTAGGTCACTAGTTG
CCTCGTCAGGCACTCTGGAGTTTATCACTGAGGGTTTCACTTGGACTGGG
GTCACTCAGAATGGGGGAAGCAATGCTTGCAAAAGGGGACCTGGTAGCGG
TTTTTTCAGTAGACTGAACTGGTTGACCAAATCAGGAAGCACATATCCAG
TGCTGAACGTGACTATGCCAAACAATGACAATTTTGACAAACTATACATT
TGGGGGGTTCACCACCCGAGCACGAACCAAGAACAAACCAGCCTGTATGT
TCAAGCATCAGGGAGAGTCACAGTCTCTACCAGGAGAAGCCAGCAAACTA
TAATCCCGAATATCGAGTCCAGACCCTGGGTAAGGGGTCTGTCTAGTAGA
ATAAGCATCTATTGGACAATACTTAAGCCGGGAGACGTACTGGTAATTAA
TAGTAATGGGAACCTAATCGCTCCTCGGGGTTATTTCAAAATGCGCACTG
GGAAAAGCTCAATAATGAGGTCAGATGCACCTATTGATACCTGTATTTCT
GAATGCATCACTCCAAATGGAAGCATTCCCAATGACAAGCCCTTTCAAAA
CGTAAACAAGATCACATATGGAGCATGCCCCAAGTATGTTAAGCAAAACA
CCCTGAAGTTGGCAACAGGGATGCGGAATGTACCAGAGAAACAAACTAGA
GGCCTATTCGGCGCAATAGCAGGTTTCATAGAAAATGGTTGGGAGGGAAT
GATAGACGGTTGGTACGGTTTCAGGCATCAAAATTCTGAGGGCACAGGAC
AAGCAGCAGATCTTAAAAGCACTCAAGCAGCCATCGACCAAATCAATGGG
AAATTGAACAGGGTAATCGAGAAGACGAACGAGAAATTCCATCAAATCGA
AAAGGAATTCTCAGAAGTAGAAGGGAGAATTCAGGACCTCGAGAAATACG
TTGAAGACACTAAAATAGATCTCTGGTCTTACAATGCGGAGCTTCTTGTC
GCTCTGGAGAATCAACATACAATTGACCTGACTGACTCGGAAATGAACAA
GCTGTTTGAAAAAACAAGGAGGCAACTGAGGGAAAATGCTGAAGACATGG
GCAATGGTTGCTTCAAAATATACCACAAATGTGACAACGCTTGCATAGAG
TCAATCAGAAATGGGACTTATGACCATGATGTATACAGAGACGAAGCATT
AAACAACCGGTTTCAGATCAAAGGTGTTGAACTGAAGTCTGGATACAAAG
ACTGGATCCTGTGGATTTCCTTTGCCATATCATGCTTTTTGCTTTGTGTT
GTTTTGCTGGGGTTCATCATGTGGGCCTGCCAGAGAGGCAACATTAGGTG
CAACATTTGCATTTGAGTGTATTAGTAATTA

SEQ ID NO: 11: Amino acid

MKTIIALSYIFCLALGQDLPGNDNSTATLCLGHHAVPNGTLVKT
ITDDQIEVTNATELVQSSSTGKICNNPHRILDGIDCTLIDALLGDPHCDV
FQNETWDLFVERSKAFSNCYPYDVPDYASLRSLVASSGTLEFITEGFTWT
GVTQNGGSNACKRGPGSGFFSRLNWLTKSGSTYPVLNVTMPNNDNFDKLY
IWGVHHPSTNQEQTSLYVQASGRVTVSTRRSQQTIIPNIESRPWVRGLSS

TABLE 2-continued nucleotide and amino acid sequences of the codon optimized genes and the proteins they express (not codon optimized).

RISLYWTIVKPGDVLVINSNGNLIAPRGYFKMRTGKSSIMRSDAPIDTCI
SECITPNGSIPNDKPFQNVNKITYGACPKYVKQNTLKLATGMRNVPEKQT
RGLFGAIAGFIENGWEGMIDGWYGFRHQNSEGTGQAADLKSTQAAIDQIN
GKLNRVIEKTNEKFHQIEKEFSEVEGRIQDLEKYVEDTKIDLWSYNAELL
VALENQHTIDLTDSEMNKLFEKTRRQLRENAEDMGNGCFKIYHKCDNACI
ESIRNGTYDHDVYRDEALNNRFQIKGVELKSGYKDWILWISFAISCFLLC
VVLLGFIMWACQRGNIRCNICI

NA H3N2 Acc. No.: AB295606: A/Aichi/2/1968(H3N2)
SEQ ID NO: 12: Nucleotide

GAAAATGAATCCAAATCAAAAGATAATAACAATTGGCTCTGTCTCTCTCA
CCATTGCAACAGTATGCTTCCTCATGCAGATTGCCATCCTGGTAACTACT
GTAACATTGCATTTTAAGCAATATGAGTGCGACTCCCCCGCGAGCAACCA
AGTAATGCCGTGTGAACCAATAATAATAGAAAGGAACATAACAGAGATAG
TGTATTTGAATAACACCACCATAGAGAAAGAGATATGCCCCAAAGTAGTG
GAATACAGAAATTGGTCAAAGCCGCAATGTCAAATTACAGGATTTGCACC
TTTTTCTAAGGACAATTCAATCCGGCTTTCTGCTGGTGGGGACATTTGGG
TGACGAGAGAACCTTATGTGTCATGCGATCATGGCAAGTGTTATCAATTT
GCACTCGGGCAGGGGACCACACTAGACAACAAACATTCAAATGACACAAT
ACATGATAGAATCCCTCATCGAACCCTATTAATGAATGAGTTGGGTGTTC
CATTTCATTTAGGAACCAGGCAAGTGTGTATAGCATGGTCCAGCTCAAGT
TGTCACGATGGAAAAGCATGGCTGCATGTTTGTATCACTGGGGATGACAA
AAATGCAACTGCTAGCTTCATTTATGACGGGAGGCTTGTGGACAGTATTG
GTTCATGGTCTCAAAATATCCTCAGAACCCACGAGTCGGAATGCGTTTGT
ATCAATGGGACTTGCACACTAGTAATGACTGATGGAAGTGCTTCAGGAAG
AGCCGATACTAGAATACTATTCATTGAAGAGGGGAAAATTGTCCATATTA
GCCCATTGTCAGGAAGTGCTCAGCATGTAGAAGAGTGTTCCTGTTATCCT
AGATATCCTGGCGTCAGATGTATCTGCAGAGACAACTGGAAAGGCTCTAA
TAGGCCCGTCGTAGACATAAATATGGAAGATTATAGCATTGATTCCAGTT
ATGTGTGCTCAGGGCTTGTTGGCGACACACCTAGAAACGACGACAGATCT
AGCAATAGCAATTGCAGGAATCCTAATAATGAGAGAGGGAATCAAGGAGT
GAAAGGCTGGGCCTTTGACAATGGAGATGACGTGTGGATGGGAAGAACGA
TCAGCAAGGATTTACGCTCAGGTTATGAAACTTTCAAAGTCATTGGTGGT
TGGTCCACACCTAATTCCAAATCGCAGATCAATAGACAAGTCATAGTTGA
CAGCGATAATCGGTCAGGTTACTCTGGTATTTTCTCTGTTGAGGGCAAAA
GCTGCATCAATAGGTGCTTTTATGTGGAGTTGATAAGGGGAAGGAAACAG
GAGACTAGAGTGTGGTGGACCTCAAACAGTATTGTTGTGTTTTGTGGCAC
TTCAGGTACCTATGGAACAGGCTCATGGCCTGATGGGGCGAACATCAATT
TCATGCCTATATAAGCTTTCGCAATTTTAGA

SEQ ID NO: 13: Amino acid

MNPNQKIITIGSVSLTIATVCFLMQIAILVTTVTLHFKQYECDS
PASNQVMPCEPIIIERNITEIVYLNNTTIEKEICPKVVEYRNWSKPQCQI
TGFAPFSKDNSIRLSAGGDIWVTREPYVSCDHGKCYQFALGQGTTLDNKH
SNDTIHDRIPHRTLLMNELGVPFHLGTRQVCIAWSSSSCHDGKAWLHVCI
TGDDKNATASEIYDGRLVDSIGSWSQNILRTQESECVCINGTCTVVMTDG
SASGRADTRILFIEEGKIVHISPLSGSAQHVEECSCYPRYPGVRCICRDN
WKGSNRPVVDINMEDYDIDSSYVCSGLVGDTPRNDDRSSNSNCRNPNNER
GNQGVKGWAFDNGDDVWMGRTISKDLRSGYETFKVIGGWSTPNSKSQINR
QVIVDSDNRSGYSGIFSVEGKSCINRCFYVELIRGRKQETRVWWTSNSIV
VFCGTSGTYGTGSWPDGANINFMPI

HA H2N2 Acc. No.: CY022013: A/Albany/20/1957(H2N2)
SEQ ID NO: 14: Nucleotide

ATAGACAACCAAAAGCAAAACAATGGCCATCATTTATCTCATTCTCCTGT
TCACAGCAGTGAGAGGGGACCAGATATGCATTGGATACCATGCCAATAAT
TCCACAGAGAAGGTCGACACAATTCTAGAGCGGAACGTCACTGTGACTCA
TGCCAAGGACATTCTTGAGAAGACCCATAACGGAAAGTTATGCAAACTAA
ACGGAATCCCTCCACTTGAACTAGGGGACTGTAGCATTGCCGGATGGCTC
CTTGGAAATCCAGAATGTGATAGGCTTCTAAGTGTGCCAGAATGGTCCTA
TATAATGGAGAAAGAAAACCCGAGAGACGGTTTGTGTTATCCAGGCAGCT
TCAATGATTATGAAGAATTGAAACATCTCCTCAGCAGCGTGAAACATTTC
GAGAAAGTAAAGATTCTGCCCAAAGATAGATGGACACAGCATACAACAAC
TGGAGGTTCACGGGCCTGCGCGGTGTCTGGTAATCCATCATTCTTCAGGA
ACATGATCTGGCTGACAAAGAAAGGATCAAATTATCCGGTTGCCAAAGGA
TCGTACAACAATACAAGCGGAGAACAAATGCTAATAATTTGGGGGGTGCA
CCATCCCAATGATGAGACAGAACAAAGAACATTGTACCAGAATGTGGGAA
CCTATGTTTCCGTAGGCACATCAACATTGAACAAAAGGTCAACCCCAGAC
ATAGCAACAAGGCCTAAAGTGAATGGACTAGGAAGTAGAATGGAATTCTC
TTGGACCCTATTGGATATGTGGGACACCATAAATTTTGAGAGTACTGGTA
ATCTAATTGCACCAGAGTATGGATTCAAAATATCGAAAAGAGGTAGTTCA
GGGATCATGAAAACAGAAGGAACACTTGGGAACTGTGAGACCAAATGCCA
AACTCCTTTGGGAGCAATAAATACAACATTGCCTTTTCACAATGTCCACC

TABLE 2-continued nucleotide and amino acid sequences of the codon optimized genes and the proteins they express (not codon optimized).

```
CACTGACAATAGGTGAGTGCCCCAAATATGTAAAATCGGAGAAGTTGGTC
TTAGCAACAGGACTAAGGAATGTTCCCCAGATTGAATCAAGAGGATTGTT
TGGGGCAATAGCTGGTTTTATAGAAGGAGGATGGCAAGGAATGGTTGATG
GTTGGTATGGATACCATCACAGCAATGACCAGGGATCAGGGTATGCAGCG
GACAAAGAATCCACTCAAAAGGCATTTGATGGAATCACCAACAAGGTAAA
TTCTGTGATTGAAAAGATGAACACCCAATTTGAAGCTGTTGGGAAAGAAT
TCAGTAACTTAGAGAGAAGACTGGAGAACTTGAACAAAAAGATGGAAGAC
GGGTTTCTAGATGTGTGGACATACAATGCTGAGCTTCTAGTTCTGATGGA
AAATGAGAGGACACTTGACTTTCATGATTCTAATGTCAAGAATCTGTATG
ATAAAGTCAGAATGCAGCTGAGAGACAACGTCAAAGAACTAGGAAATGGA
TGTTTTGAATTTTATCACAAATGTGATGATGAATGCATGAATAGTGTGAA
AAACGGGACGTATGATTATCCCAAGTATGAAGAAGAGTCTAAACTAAATA
GAAATGAAATCAAAGGGGTAAAATTGAGCAGCATGGGGGTTTATCAAATC
CTTGCCATTTATGCTACAGTAGCAGGTTCTCTGTCACTGGCAATCATGAT
GGCTGGGATCTCTTTCTGGATGTGCTCCAACGGGTCTCTGCAGTGCAGGA
TCTGCATATGATTATAAGTCATTTTATAATTAA
```

SEQ ID NO: 15: Amino acid

```
MAIIYLILLFTAVRGDQICIGYHANNSTEKVDTILERNVTVTHA
KDILEKTHNGKLCKLNGIPPLELGDCSIAGWLLGNPECDRLLSVPEWSYI
MEKENPRDGLCYPGSFNDYEELKHLLSSVKHFEKVKILPKDRWTQHTTTG
GSRACAVSGNPSFFRNMIWLTKKGSNYPVAKGSYNNTSGEQMLIIWGVHH
PNDETEQRTLYQNVGTYVSVGTSTLNKRSTPDIATRPKVNGLGSRMEFSW
TLLDMWDTINFESTGNLIAPEYGFKISKRGSSGIMKTEGTLGNCETKCQT
PLGAINTTLPFHNVHPLTIGECPKYVKSEKLVLATGLRNVPQIESRGLFG
AIAGFIEGGWQGMVDGWYGYHHSNDQGSGYAADKESTQKAFDGITNKVNS
VIEKMNTQFEAVGKEFSNLERRLENLNKKMEDGFLDVWTYNAELLVLMEN
ERTLDFHDSNVKNLYDKVRMQLRDNVKELGNGCFEFYHKCDDECMNSVKN
GTYDYPKYEEESKLNRNEEKGVKLSSMGVYQILAIYATVAGSLSLAIMMA
GISFWMCSNGSLQCRICI
```

NA H2N2 Acc. No.: CY022015: A/Albany/20/1957(H2N2)
SEQ ID NO: 16: Nucleotide

```
TGAAAATGAATCCAAATCAAAAGATAATAACAATTGGCTCTGTCTCTCTC
ACCATTGCAACAGTATGCTTCCTCATGCAGATTGCCATCCTGGCAACTAC
TGTGACATTGCATTTTAAACAACATGAGTGCGACTCCCCCGCGAGCAACC
AAGTAATGCCATGTGAACCAATAATAATAGAAAGGAACATAACAGAGATA
GTGTATTTGAATAACACCACCATAGAGAAAGAGATTTGCCCCGAAGTAGT
GGAATACAGAAATTGGTCAAAGCCGCAATGTCAAATTACAGGATTTGCAC
CTTTTTCTAAGGACAATTCAATCCGGCTTTCTGCTGGTGGGGACATTTGG
GTGACGAGAGAACCTTATGTGTCATGCGATCCTGGCAAGTGTTATCAATT
TGCACTCGGGCAAGGGACCACACTAGACAACAAACATTCAAATGGCACAA
TACATGATAGAATCCCTCACCGAACCCTATTAATGAATGAGTTGGGTGTT
CCATTTCATTTAGGAACCAAACAAGTGTGTGTAGCATGGTCCAGCTCAAG
TTGTCACGATGGAAAAGCATGGTTGCATGTTTGTGTCACTGGGGATGATA
GAAATGCGACTGCCAGCTTCATTTATGACGGGAGGCTTGTGGACAGTATT
GGTTCATGGTCTCAAAATATCCTCAGGACCCAGGAGTCGGAATGCGTTTG
TATCAATGGGACTTGCACAGTAGTAATGACTGATGGAAGTGCATCAGGAA
GAGCCGATACTAGAATACTATTCATTAAAGAGGGCAAAATTGTCCATATC
AGCCCATTGTCAGGAAGTGCTCAGCATATAGAGGAGTGTTCCTGTTACCC
TCGATATCCTGACGTCAGATGTATCTGCAGAGACAACTGGAAAGGCTCTA
ATAGGCCCGTTATAGACATAAATATGGAAGATTATAGCATTGATTCCAGT
TATGTGTGCTCAGGGCTTGTTGGCGACACACCCAGGAACGACGACAGCTC
TAGCAATAGCAATTGCAGGGATCCTAACAATGAGAGAGGGAATCCAGGAG
TGAAAGGCTGGGCCTTTGACAATGGAGATGATGTATGGATGGGAAGAACA
ATCAACAAAGATTCACGCTCAGGTTATGAAACTTTCAAAGTCATTGGTGG
TTGGTCCACACCTAATTCCAAATCGCAGGTCAATAGACAGGTCATAGTTG
ACAACAATAATTGGTCTGGTTACTCTGGTATTTTCTCTGTTGAGGGCAAA
AGCTGCATCAATAGGTGCTTTTATGTGGAGTTGATAAGGGGAAGGCCACA
GGAGACTAGAGTATGGTGGACCTCAAACAGTATTGTTGTGTTTTGTGGCA
CTTCAGGTACTTATGGAACAGGCTCATGGCCTGATGGGGCGAACATCAAT
TTCATGCCTATATAAGCTTTCGCAATTTTAGAAAA
```

SEQ ID NO: 17: Amino acid

```
MNPNQKIITIGSVSLTIATVCFLMQIAILATTVTLHFKQHECDS
PASNQVMPCEPIIIERNITEIVYLNNTTIEKEICPEVVEYRNWSKPQCQI
TGFAPFSKDNSIRLSAGGDIWVTREPYVSCDPGKCYQFALGQGTTLDNKH
SNGTIHDRIPHRTLLMNELGVPFHLGTKQVCVAWSSSSCHDGKAWLHVCV
TGDDRNATASFIYDGRLVDSIGSWSQNILRTQESECVCINGTCTVVMTDG
SASGRADTRILFIKEGKIVHISPLSGSAQHIEECSCYPRYPDVRCICRDN
WKGSNRPVIDINMEDYSIDSSYVCSGLVGDTPRNDDSSSNSNCRDPNNER
GNPGVKGWAFDNGDDVWMGRTINKDSRSGYETFKVIGGWSTPNSKSQVNR
QVIVDNNNWSGYSGIFSVEGKSCINRCFYVELIRGRPQETRVWWTSNSIV
VFCGTSGTYGTGSWPDGANINFMPI
```

In one embodiment, a method of treating or preventing infection with a H1, H2, H3 containing influenza A in a subject is provided, comprising delivering to the subject a naked DNA and/or RNA molecule encoding hemagglutinin (HA) from pandemic influenza selected from one or more of the 1918 H1N1, the 1957 H2N2, and the 1968 H3N2 influenza A virus. In a further embodiment, the method comprises administering a vaccine for N1, N2 containing influenza A in humans or swine, the method further comprising delivering to the subject a naked DNA and/or RNA molecule encoding neuraminidase (NA) and/or matrix protein (M) and/or the nucleoprotein (NP) from a pandemic influenza virus therapeutically or prophylactically.

In another embodiment, the codons of the DNA or RNA may be humanized using codons of highly expressed human proteins. In yet another embodiment, an adjuvant is delivered to the subject. In still a further embodiment, a DNA vaccine is administered by saline injection of naked DNA and/or RNA, inoculated by gene gun or is delivered coupled to particles.

Also provided is a vaccine for human use containing a naked DNA and/or RNA molecule encoding hemagglutinin (HA) from a pandemic influenza selected from the 1918 H1N1, the 1957 H2N2, and the 1968 H3N2 influenza A virus. In a further embodiment, the vaccine also comprises a naked DNA and/or RNA molecule encoding neuraminidase (NA) and/or matrix protein (M) and/or the nucleoprotein (NP) from a pandemic influenza virus.

In another embodiment, the vaccine's antigenic component consists of the HA and one or more of a neuraminidase (NA), a matrix (M) protein, and/or nucleoprotein (NP). The vaccine's antigenic component may also consist of naked DNA or RNA molecule coding for the HA and one or more of a neuraminidase (NA) protein, matrix protein, and/or nucleoprotein (NP). In still a further embodiment, the DNA or RNA codons may be humanized using codons of highly expressed human proteins. In yet another embodiment, the vaccine contains an adjuvant.

In another embodiment, a vaccine described herein may be administered therapeutically to already infected humans or swine.

In one embodiment, a method of treating or preventing infection with H5, H7 or H2 containing influenza A in a subject is provided, wherein a naked DNA and/or RNA molecule encoding hemagglutinin (HA) and/or neuraminidase (NA) from an influenza strain selected from the group consisting of a 2001 H5N7 low pathogenic Avian influenza virus (AIV) strain (A/Mallard/Denmark/64650/03(H5N7)) and a March 2006 Denmark H5N1 high pathogenic AIV strain (A/buzzard/Denmark/6370/06(H5N1)) is delivered to a subject. In a further embodiment, the naked DNA and/or RNA molecule encoding HA or NA are delivered in a composition containing the HA and/or NA proteins. In another embodiment, the HA or NA are delivered in a composition containing the naked DNA and/or RNA molecule encoding the HA and/or NA proteins. In still another embodiment, the DNA or RNA codons are humanized.

In another embodiment, a vaccine for preventing infection with H5, H7 or H2 containing influenza A infections in humans or swine is provided, the vaccine containing a naked DNA and/or RNA molecule encoding hemagglutinin (HA) and/or neuraminidase (NA) from an influenza strain selected from the group consisting of 2001 H5N7 low pathogenic Avian influenza virus (AIV) strain (A/Mallard/Denmark/64650/03(H5N7)), March 2006 Denmark H5N1 high pathogenic AIV strain (A/buzzard/Denmark/6370/06(H5N1)), (A/duck/Denmark/53-147-8/08 (H7N1)) and (A/widegeon/Denmark/66174/G18/04 (H2N3)). In a further embodiment, the vaccine contains naked DNA and/or RNA molecules encoding the HA or NA proteins. In another embodiment, the DNA or RNA codons are humanized. In still another embodiment, the vaccine further contains an adjuvant.

The following examples are illustrative of the compositions and methods of the invention. It will be readily understood by one of skill in the art that the specific conditions described herein can be varied without departing from the scope of the present invention. It will be further understood that other compositions not specifically illustrated are within the scope of the invention as defined herein.

EXAMPLES

Example 1

Construction of Expression Vectors

The 1918 pandemic H1N1 genes were designed from nucleotide sequences published in GenBank (HA: A/South Carolina/1/18 AF117241, and NA, NP and M: A/Brevig Mission/1/18 AF250356, AY744035 and AY130766, respectively). The genes were made synthetically and designed to include the appropriate restriction enzymes and Kozak sequence (GCCACC), −1 base upstream from the start codon, for efficient cloning and transcription in the WRG7079 expression vector (PowderJect, Madison, Wis.). The genes were synthesised using only codons from highly expressed human genes (5) (codon optimised). By this the nucleotide codons are altered (humanised), but the encoded amino acids are identical to those encoded by the viral RNA. The genes were further cloned individually into the WRG7079 expression vector. Key elements in the expression vector are a kanamycin resistance gene, cytomegalovirus immediate-early promoter, intron A, and polyadenylation signal. The tissue plasminogen activator (tPA) signal sequence in the original WRG7079 expression vector, used to target proteins to a secretory pathway, was excised in favour of the influenza signal sequence located in the 1918 HA and NA genes. The same vector was also applied for expression of the internal genes NP and M1 that do not have secretory signals, and which are naturally located inside the virus and inside the infected cells; therefore the tPA secretory signal of the WRG7079 was removed. The WRG7079 was further modified to remove an unwanted app109 nucleotide sequence from the SIV nef gene.

Viral RNA from the A/New Caledonia/20/99(H1N1) MDCK cell cultivated virus was isolated by QIAamp® Viral RNA Mini Kit (QIAGEN, Hilden, Germany) and RT-PCR was performed as previously described (2) by OneStep® RT-PCR Kit (QIAGEN). The primers were designed to amplify the coding gene of HA and NA. The same restriction sites and Kozak sequence were included in the primers as for the 1918 H1N1 constructs (HA NC F: 5'-caacgcgtgccaccatgaaagcaaaactactgg-3' (SEQ ID NO:18), HA NC R: 5'-tcggcgcctcagatgcatattctacactgc-3' (SEQ ID NO:19), NA NC F: 5'-caacgcgtgccaccatgaatccaaatc-3' (SEQ ID NO:20), NA NC R: 5'-tcg gcgccctacttgtcaatggtgaa cggc-3' (SEQ ID NO:21)). The RT-PCR products were purified from an agarose gel by the GFX™ PCR DNA and Gel Band Purification Kit (Amersham Biosciences, Piscataway, USA) prior to sequencing.

Purified PCR products were sequenced directly. The sequencing reaction was performed by ABI PRISM® BigDye™ Terminators v3.1 Cycle Sequencing Kit (Applied Biosystems, Foster City, Calif., USA) as described previously (2). The development of the sequences was performed on an automatic ABI PRISM® 3130 genetic analyzer (Applied Biosystems) with 80 cm capillaries. Consensus sequences were generated in SeqScape® Software v2.5 (Applied Biosystems). Sequence assembly, multiple alignment and alignment trimming were performed with the BioEdit software v.7.0.5 9. The PCR products were further restriction enzyme digested and cloned into the WRG7079 expression vector in DH5a bacteria. Endotoxin free DNA purification of the vaccine clones were prepared by EndoFree Plasmid Giga Kit (QIAGEN). All inserts and vaccine clones were control sequenced.

Example 2

Immunisations

A total of 24 ferrets (Mustela Putorius Furo), approximately seven months old, were divided in four groups by using a chip-tag identification for dogs (E-vet, pet-id, Haderslev, Denmark), six animals in each group. All animals were kept together and fed a standard diet with food and water ad libitum. The animals were housed according to the Danish Animal Experimentation Act and kept at level II biosecurity facilities at the Faculty of Life Sciences, Copenhagen. The acclimatisation period was nine days.

Four groups of six ferrets were vaccinated as follows; (1) HA (codon optimised gene) and NA (codon optimised gene) 1918 H1N1 plasmid DNA vaccinated, (2) HA, NA, NP and M (all codon optimised) 1918 H1N1 plasmid DNA vaccinated, (3) empty plasmid vaccinated (negative vaccine control) and (4) HA and NA (not codon optimised) A/New Caledonia/20/99(H1N1) plasmid DNA vaccinated (positive vaccine control). All ferrets received four standard gene gun shots onto shaved abdomen. HA and NA DNA mixed vaccines were given in two shots and NP and M DNA mixed vaccines were given in two shots. Therefore groups 1 and 4 receiving only HA and NA DNA vaccine were additionally shot twice with empty plasmid DNA, ensuring that all animals had received the same amount of DNA and the same number of shots. The ferrets were gene gun (Helios, Bio-Rad, Hercules, Calif.) inoculated (400 psi compressed helium) on shaved abdominal skin, using 2 ng plasmid DNA-coated gold particles (1.6 μm-sized particles), 80-95% coating efficiency each shot. Each ferret received four shots, three times biweekly. Ferrets were challenged ten days after the third immunisation by $1\times10^7$ 50% egg infectious dose (EID50) of A/New Caledonia/20/99(H1N1) virus in 100 μl PBS administrated into the nostrils with a syringe. Blood serum was collected at day −2,3,5 and 7 post-challenge from *vena jugularis* of anesthetised animals (tiletamine/zolazepam (zoletil-mix for cats)). Animals were terminated with pentobarbital.

Example 3

Quantitative Real Time RT-PCR Assay for Influenza A

At the day of blood serum collection the nostrils of each ferret were flushed with 1 ml PBS and the flushing were frozen down immediately for real-time RT-PCR analysis. Two hundred micro litres of nasal wash were extracted on an automated MagNA Pure LC Instrument applying the MagNa Pure LC Total Nucleic Acid Isolation Kit (Roche diagnostics, Basel, Switzerland). The extracted material was eluated in 200 µl Milli-Q H2O. The RT-PCR reactions were performed with oligonucleotide sequences as described by Spackman et al., (23). Extracted material (5 µl) was added to 20 µl of master mix consisting of 10 nM of each primer and 2 nM of the Taqman probe labelled with FAM in the 5' end and black hole quencher 1 in the 3' end together with reagents from the OneStep® RT-PCR Kit (QIAGEN, Hilden, Germany) according to the manufacturer. Target sequences were amplified on the MX3005 system from Stratagene with the following program: 20 min 50° C., 15 min 95° C. and 40 cycles of 15 sec 95° C. and 60 sec at 55° C. The content of viral genomes in the samples was determined using a standard curve developed by amplifying dilution of H1N1 with known concentration.

Example 4

Serum Antibody Determined by ELISA

ELISA plates (96 wells) were coated with 100 µl, split influenza vaccine (Vaxigrip, Sanofi Pasteur, Belgium) diluted 1:100 in 35 mM $NaHCO_3$ pH 9.6 and 15 mM $Na_2CO_3$ overnight at 4° C. Wells were blocked with 1% PBS/BSA for 30 minutes at room temperature. Plates were washed with 0.05% PBS/tween (PBST). Sera 1:100 were diluted in 0.1% BSA/PBST two-folds in the plate and incubated for one hour at room temperature. The plates were washed and incubated with 100 µl biotinylated rabbit anti-ferret IgG diluted 1:250 for one hour in room temperature, washed, and incubated with 100 µl 1:1,000 horseradish peroxidase (HRP) streptavidin (DakoCytomation, Glostrup, Denmark). After 30 minutes the plates were washed and 100 µl of hydrogen peroxide with OPD was added. The reaction was stopped by adding 50 µl 0.5 M $H_2SO_4$ and read at OD492 nm.

Example 5

Results

Ferrets were negative for influenza specific antibodies seven days before start of immunisations as measured by ELISA.

Figure 1B:
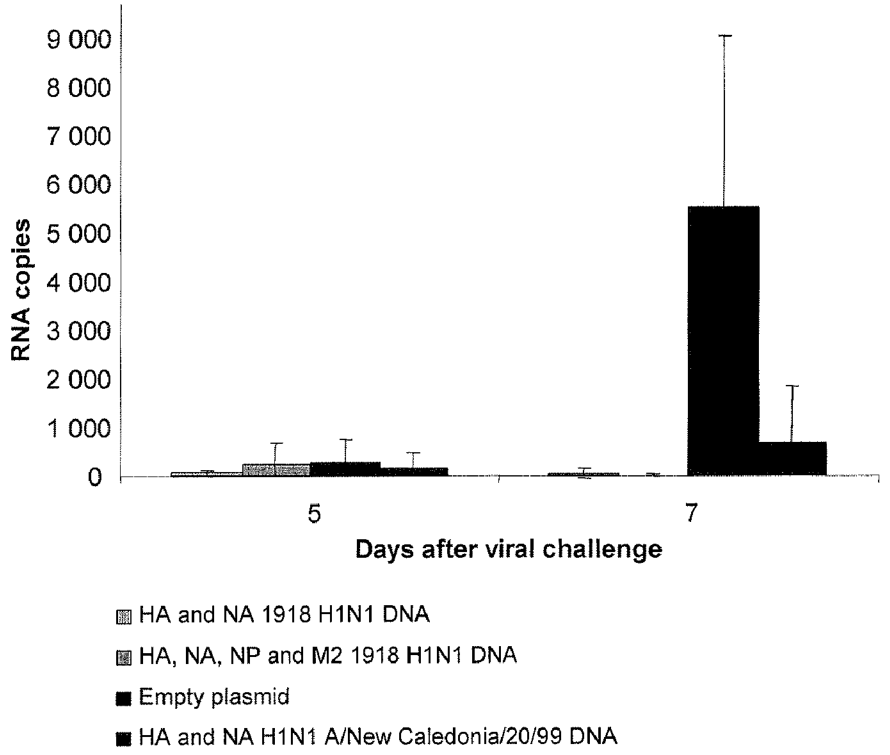
FIG. 1B illustrates the number of viral RNA copies (real time RT/PCR) in nasal wash in days after challenge. Six ferrets were in each group.

High IgG specific serum antibodies (to A/New Caledonia/20/99(H1N1) in ELISA) were observed at day seven post-challenge in ferrets vaccinated with both HA+NA 1918 (two plasmids) and HA+NA+NP+M 1918 DNA vaccines (four plasmids) (FIG. 1). Ferrets vaccinated with HA+NA DNA A/New Caledonia/20/99(H1N1) induced lower specific serum antibody titre on day seven. It is possible that higher antibody response could have been observed at later time points if the experiment had not been terminated at day seven after challenge for practical reasons.

At day five post-challenge, the ferrets vaccinated with empty plasmid (negative vaccine control) showed high viral load in nasal washing measured as viral RNA copies in the nasal washings, indicating no protection against the viral challenge. However, ferrets vaccinated with HA+NA 1918 and HA+NA, NP+M 1918 DNA vaccines were completely protected from infection with an A/New Caledonia/20/99 (H1N1) like virus (FIG. 1). Partial protection was observed in ferrets vaccinated with HA+NA A/New Caledonia/20/99 (H1N1) DNA plasmids.

The data clearly show that DNA gene gun immunisations based on genes from the 1918 H1N1 pandemic strain induce strong specific antibody response and protect ferrets completely against infection with a H1N1 strain that has drifted by 89 years. No negative or positive effects on the humoral immune response or protection was observed by including the NP and M genes in the HA+NA DNA vaccination since the protection from infection already was already 100%.

The A/South Carolina/1/18 and A/New Caledonia/20/99 are 21.2% different in the HA1 protein and possess eight substitutions at residues involved in antigenic sites 3 (1918 to New Caledonia); Cb S83P, Sa T128V and K160N, Sb S156G, Q193H and D196N, Cal N207S and A224E.

DNA vaccines do have the ability of immune stimulatory mechanisms. This might be one reason why such good cross reactivity and protection was induced against challenge infection. Cross-protection and cross-reactivity induced by DNA vaccines of strains differing by 11-13% in HA1 has been demonstrated by others (13-15) but not as high as the 21.2% observed in the present studies.

Example 6

1918 Pandemic H1N1 DNA Vaccinated Ferrets were Challenged with 2007 H1N1

Vaccine production and vaccinations and assays were carried out as described above.

Figure 2A:
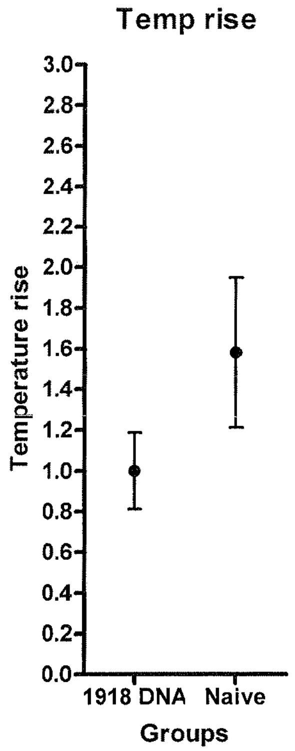
FIGS. 2A-2D provide results of 1918 pandemic H1N1 DNA vaccinated ferrets challenged with 2007 H1N1.
Figure 2B:
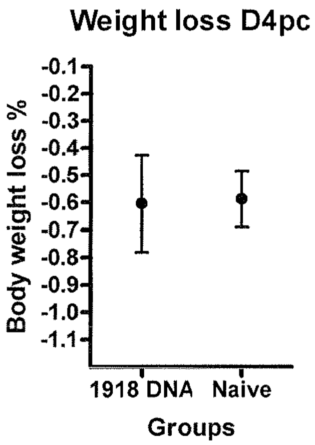
Figure 2C:
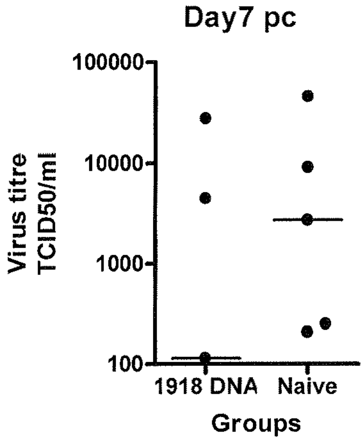
Figure 2D:
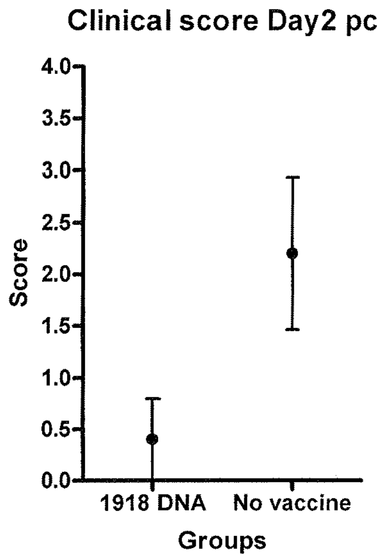

A total of 10 ferrets (Mustela Putorius Euro), approximately seven months old, were divided in two groups by using a chip-tag identification for dogs (E-vet, pet-id, Haderslev, Denmark), five animals in each group. All animals were kept together and fed a standard diet with food and water ad libitum. The animals were housed according to the Danish Animal Experimentation Act and kept at level II biosecurity facilities at the Faculty of Life Sciences, Copenhagen. The acclimatisation period was one day. Two groups of five ferrets were vaccinated as follows; (1) HA (codon optimised gene) and NA (codon optimised gene) 1918 H1N1 plasmid DNA vaccinated, (2) non-vaccinated, naïve animals. HA and NA DNA mixed vaccines were given in four shots. The ferrets were gene gun (Helios, Bio-Rad, Hercules, Calif.) inoculated (400 psi compressed helium) on shaved abdominal skin, using 2 µg plasmid DNA-coated gold particles (1.6 µm-sized particles), 80-95% coating efficiency each shot. Vaccinated ferrets received four shots, three times biweekly. Ferrets were challenged ten days after third immunisation by $1\times10^7$ 50% egg infectious dose (EID50) of A/New Caledonia/20/99 (H1N1) virus in 1000 µl PBS administrated into the nostrils with a syringe. Blood serum was collected at day −48, 0, 5, 7 and 12 post-challenge from vena jugularis of anesthetised animals (tiletamine/zolazepam (zoletil-mix for cats)). Animals were terminated with pentobarbital. The 1918 DNA vaccinated ferrets had a lower temperature rise than the unvaccinated group (p=0.2) at the day of maximal temperature rise, day 2 post challenge (FIG. 2A). No difference in weight loss between the vaccinated and the unvaccinated animals was observed at the day of maximal weight loss, day 4 post challenge (FIG. 2B). Vaccinated animals displayed fewer influenza symptoms than unvaccinated animals measured by sneezing, nasal discharge and activity level (p=0.065) (FIG. 2C.). Ferrets in both groups had high virus load post infection measured by quantitative real-time RT-PCR, however by day 7 post infection the 1918 DNA vaccinated ferrets better cleared their virus infection than the unvaccinated ferrets (p=0.63) (FIG. 2D).

Example 7

Challenge with New Caledonia H1N1 in Ferrets

Traditional protein H1N1 New Caledonia vaccine plus/minus DDA/TDB adjuvants versus 1918 H1N1 HA plus NA DNA vaccine (versus empty DNA vaccine vector) using two DNA immunizations (instead or the usual 3 DNA immunizations)

Traditional protein H1N1 split vaccine (two immunizations) versus 1918 H1N1 HA plus NA codon optimized DNA vaccine versus codon optimized and non-codon-optimized New Caledonia H1N1 HA and NA versus codon optimized M and NP from 1918 H1N1 virus (versus empty DNA vaccine vector) using three immunizations.

Ferrets are challenged with H1N1 New Caledonia-like virus intra nasally and virus quantitated in basal washings by real-time RT/PCR assay. Ferret antibodies will be examined for ELISA antibodies and HI antibody reactions to H1N1, H2N2, H3N2, H5N7, and/or H5N1.

Example 8

Mouse Antibody Experiments

Codon optimized versus non-codon optimized HA and NA DNA vaccines from New Caledonia H1N1 (shows the difference between codon optimization and non-optimization) versus codon optimized HA and NA from 1918 H1N1 strain is inoculated in mice. Antibody titers and epitope mapping of induced antibodies is done by overlapping peptides in ELISA and cross-reactions measured to other influenza A virus.

Example 9

Protein Expression Experiments

Figure 3:
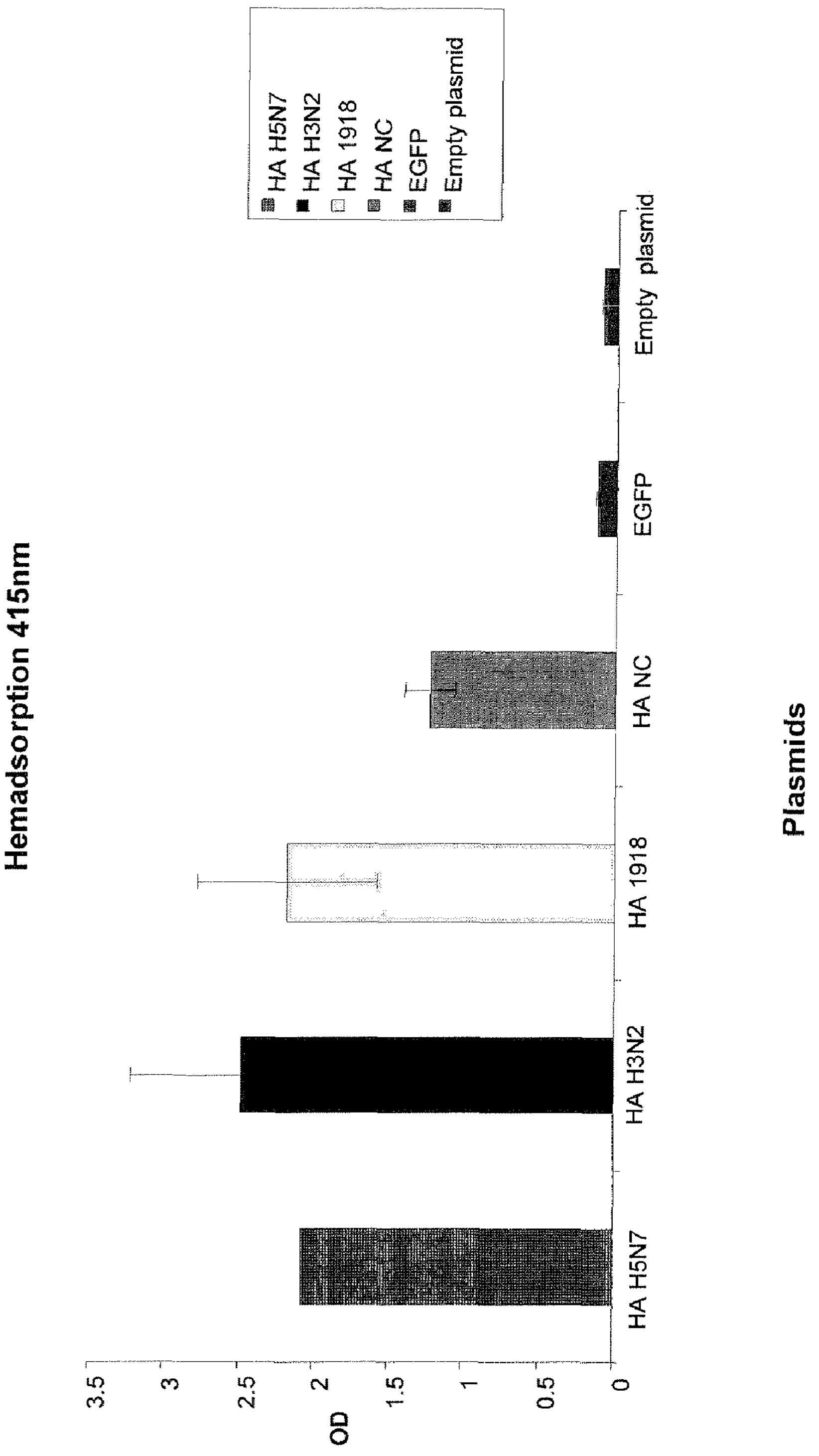
FIG. 3 is a bar chart showing hemadsorption as a measure of functional protein expression in mammalian cells of codon optimized HA from 1918 H1N1(HA 1918), avian H5N7 (HA H5N7) and 1968 H3N2 (HA H3N2) compared to non-codon optimized 1918 H1N1 (HA NC).

Codon optimized versus non-codon optimized HA and NA DNA vaccines from New Calidonia H1N1 (shows the difference between codon optimization and non-optimization) versus codon optimized HA and NA from 1918 H1N1 strain is expressed in mammalian cell lines in vitro and standard radio immuno precipitation (RIPA) are done with polyclonal influenza A antibodies to examine the improved protein expression obtained by codon optimization. Codon optimized from 1918 H1N1, H5N7 and H3N2 strain versus non-codon optimized HA DNA vaccines from 1918 H1N1 strain is expressed in mammalian cell lines in vitro and hemadsorption is measured. This shows that the H1 is functionally expressed better when codons are optimized (FIG. 3).

Example 10

Cytokine Induction Experiments

Codon optimized versus non-codon optimized HA and NA DNA vaccines from New Caledonia H1N1 (shows the difference between codon optimization and non-optimization) versus codon optimized HA and NA from 1918 H1N1 strain is added onto mammalian peripheral blood monocytes (PBMCs) in vitro and measurements of resulting cytokine production is measured in the cell supernatant to examine the innate immune induction (adjuvant effect) obtained by codon optimization and by the codon optimised H1N1 1918 HA and NA as compared to the codon optimised H1N1 New Caledonia HA and NA to examine special cytokine induction by the 1918 genes.

Example 11

1918 HA and NA Protein Vaccine Experiments

Proteins are produced by the DNA vaccine plasmids and used as a protein vaccine in mice or ferrets as compared to DNA vaccination and to traditional protein split vaccine to measure the immune induction of 1918 proteins versus DNA vaccine.

Example 12

Mouse DNA Vaccine Delivery Experiments

Codon optimized HA and/or NA DNA vaccines from 1918 H1N1 strain is inoculated in mice as expression plasmids or as a linear piece of DNA containing the necessary components for vaccine gene expression but without the rest of the plasmid to rule out any effect of the rest of the plasmid.

Example 13

Swine DNA Vaccine Delivery Experiments

Codon optimized HA and/or NA DNA vaccines from 1918 H1N1 strain is inoculated in pigs as expression plasmids and challenge with a present day New Caledonia-like H1N1 strain and protection against disease and immune induction are measured.

References

1. Antonovics, J., M. E. Hood, and C. H. Baker. 2006. Molecular virology: Was the 1918 flu avian in origin? Nature 440:E9.
2. Bragstad, K., P. H. Jorgensen, K. J. Handberg, S. Mellergaard, S. Corbet, and A. Fomsgaard. 2005. New avian influenza A virus subtype combination H5N7 identified in Danish mallard ducks. Virus. Res. 109:181-190.
3. Caton, A. J., G. G. Brownlee, J. W. Yewdell, and W. Gerhard. 1982. The antigenic structure of the influenza virus A/PR/8/34 hemagglutinin (H1 subtype). Cell 31:417-427.
4. Chen, Z., S. e. Kadowaki, Y. Hagiwara, T. Yoshikawa, K. Matsuo, T. Kurata, and S. I. Tamura. 2000. Cross-protection against a lethal influenza virus infection by DNA vaccine to neuraminidase. Vaccine 18:3214-3222.
5. Corbet, S., L. Vinner, D. M. Hougaard, K. Bryder, H. V. Nielsen, C. Nielsen, and A. Fomsgaard. 2000. Construction, biological activity, and immunogenicity of synthetic envelope DNA vaccines based on a primary, CCR5-tropic, early HIV type 1 isolate (BX08) with human codons. AIDS Res. Hum. Retroviruses 16:1997-2008.
6. Davis, H. L., B. A. Demeneix, B. Quantin, J. Coulombe, and R. G. Whalen. 1993. Plasmid DNA is superior to viral vectors for direct gene transfer into adult mouse skeletal muscle. Hum. Gene Ther. 4:733-740.
7. Donnelly, J. J., A. Friedman, D. Martinez, D. L. Montgomery, J. W. Shiver, S. L. Motzel, J. B. Ulmer, and M. A. Liu. 1995. Preclinical efficacy of a prototype DNA vaccine: enhanced protection against antigenic drift in influenza virus. Nat. Med. 1:583-587.
8. Epstein, S. L., W. p. Kong, J. A. Misplon, C. Y. Lo, T. M. Tumpey, L. Xu, and G. J. Nabel. 2005. Protection against multiple influenza A subtypes by vaccination with highly conserved nucleoprotein. Vaccine 23:5404-5410.

9. Hall, T. A. 1999. BioEdit: a user-friendly biological sequence alignment editor and analysis program for Windows 95/98/NT. Nucl. Acids. Symp. Ser 41:95-98.
10. Johnson, N. P. and J. Mueller. 2002. Updating the accounts: global mortality of the 1918-1920 “Spanish” influenza pandemic. Bull. Hist Med 76:105-115.
11. Kawaoka, Y., S. Krauss, and R. G. Webster. 1989. Avian-to-human transmission of the PB1 gene of influenza A viruses in the 1957 and 1968 pandemics. J Virol 63:4603-4608.
12. Kobasa, D., A. Takada, K. Shinya, M. Hatta, P. Halfmann, S. Theriault, H. Suzuki, H. Nishimura, K. Mitamura, N. Sugaya, T. Usui, T. Murata, Y. Maeda, S. Watanabe, M. Suresh, T. Suzuki, Y. Suzuki, H. Feldmann, and Y. Kawaoka. 2004. Enhanced virulence of influenza A viruses with the haemagglutinin of the 1918 pandemic virus. Nature 431:703-707.
13. Kodihalli, S., H. Goto, D. L. Kobasa, S. Krauss, Y. Kawaoka, and R. G. Webster. 1999. DNA vaccine encoding hemagglutinin provides protective immunity against H5N1 influenza virus infection in mice. J. Virol. 73:2094-2098.
14. Kodihalli, S., J. R. Haynes, H. L. Robinson, and R. G. Webster. 1997. Cross-protection among lethal H5N2 influenza viruses induced by DNA vaccine to the hemagglutinin. J. Virol. 71:3391-3396.
15. Kodihalli, S., D. L. Kobasa, and R. G. Webster. 2000. Strategies for inducing protection against avian influenza A virus subtypes with DNA vaccines. Vaccine 18:2592-2599.
16. Kong, W. p., C. Hood, Z. y. Yang, C. J. Wei, L. Xu, A. Garcia-Sastre, T. M. Tumpey, and G. J. Nabel. 2006. Protective immunity to lethal challenge of the 1918 pandemic influenza virus by vaccination. PNAS 103:15987-15991.
17. Lindstrom, S. E., N. J. Cox, and A. Klimov. 2004. Genetic analysis of human H2N2 and early H3N2 influenza viruses, 1957-1972: evidence for genetic divergence and multiple reassortment events. Virology 328:101-119.
18. Ljungberg, K., C. Kolmskog, B. Wahren, G. van Amerongen, M. Baars, A. Osterhaus, A. Linde, and G. Rimmelzwaan. 2002. DNA vaccination of ferrets with chimeric influenza A virus hemagglutinin (H3) genes. Vaccine 20:2045-2052.
19. Reid, A. H., T. G. Fanning, J. V. Hultin, and J. K. Taubenberger. 1999. Origin and evolution of the 1918 “Spanish” influenza virus hemagglutinin gene. Proc. Natl. Acad. Sci. U.S. A 96:1651-1656.
20. Reid, A. H., T. G. Fanning, T. A. Janczewski, and J. K. Taubenberger. 2000. Characterization of the 1918 “Spanish” influenza virus neuraminidase gene. Proc. Natl. Acad. Sci. U.S. A 97:6785-6790.
21. Seo, S. H., E. Hoffmann, and R. G. Webster. 2002. Lethal H5N1 influenza viruses escape host anti-viral cytokine responses. Nat. Med. 8:950-954.
22. Smith, H. and C. Sweet. 1988. Lessons for human influenza from pathogenicity studies with ferrets. Rev. Infect Dis 10:56-75.
23. Spackman, E., D. A. Senne, T. J. Myers, L. L. Bulaga, L. P. Garber, M. L. Perdue, K. Lohman, L. T. Daum, and D. L. Suarez. 2002. Development of a real-time reverse transcriptase PCR assay for type A influenza virus and the avian H5 and H7 hemagglutinin subtypes. J. Clin. Microbial. 40:3256-3260.
24. Talon, J., C. M. Horvath, R. Polley, C. F. Basler, T. Muster, P. Palese, and A. Garcia-Sastre. 2000. Activation of interferon regulatory factor 3 is inhibited by the influenza A virus NS1 protein. J. Virol. 74:7989-7996.
25. Tamura, S., T. Tanimoto, and T. Kurata. 2005. Mechanisms of broad cross-protection provided by influenza virus infection and their application to vaccines. Jpn. J. Infect Dis 58:195-207.
26. Taubenberger, J. K., A. H. Reid, R. M. Lourens, R. Wang, G. Jin, and T. G. Fanning. 2005. Characterization of the 1918 influenza virus polymerase genes. Nature 437:889-893.
27. Tumpey, T. M., C. F. Basler, P. V. Aguilar, H. Zeng, A. Solorzano, D. E. Swayne, N. J. Cox, J. M. Katz, J. K. Taubenberger, P. Palese, and A. Garcia-Sastre. 2005. Characterization of the reconstructed 1918 spanish influenza pandemic virus. Science 310:77-80.
28. Tumpey, T. M., A. Garcia-Sastre, J. K. Taubenberger, P. Palese, D. E. Swayne, and C. F. Basler. 2004. Pathogenicity and immunogenicity of influenza viruses with genes from the 1918 pandemic virus. Proc. Natl. Acad. Sci. U.S. A 101:3166-3171.
29. Tumpey, T. M., A. Garcia-Sastre, J. K. Taubenberger, P. Palese, D. E. Swayne, M. J. Pantin-Jackwood, S. Schultz-Chemy, A. Solorzano, N. Van Rooijen, J. M. Katz, and C. F. Basler. 2005. Pathogenicity of influenza viruses with genes from the 1918 pandemic virus: functional roles of alveolar macrophages and neutrophils in limiting virus replication and mortality in mice. J Virol 79:14933-14944.
30. Ulmer, J. B., T. M. Fu, R. R. Deck, A. Friedman, L. Guan, C. DeWitt, X. Liu, S. Wang, M. A. Liu, J. J. Donnelly, and M. J. Caulfield. 1998. Protective CD4+ and CD8+T cells against influenza virus induced by vaccination with nucleoprotein DNA. J Virol 72:5648-5653.
31. Wang, X., M. Li, H. Zheng, T. Muster, P. Palese, A. A. Beg, and A. Garcia-Sastre. 2000. Influenza A Virus NS1 Protein Prevents Activation of NF-kappa B and Induction of Alpha/Beta Interferon. J. Virol. 74:11566-11573.
32. Webster, R. G., E. F. Fynan, J. C. Santoro, and H. Robinson. 1994. Protection of ferrets against influenza challenge with a DNA vaccine to the haemagglutinin. Vaccine 12:1495-1498.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method of inducing an immune response to an H1N1 influenza A in a subject, said method comprising delivering to the subject (i) an isolated naked nucleic acid sequence encoding the matrix protein (M) from a pandemic influenza virus and an isolated naked nucleic acid sequence encoding the nucleoprotein (NP) from a pandemic influenza virus, and (ii) an isolated naked nucleic acid sequence encoding hemagglutinin (HA) from a pandemic influenza virus, wherein said M and NP proteins are encoded by the isolated naked nucleic acid sequences of SEQ ID Nos: 7 and 5, respectively, and the M and NP proteins are from a 1918 H1N1 influenza A virus and said HA is from a different pandemic influenza virus than that of said M and NP.

2. The method according to claim 1, wherein the immune response is a cytotoxic cellular response.

3. The method according to claim 1, wherein the immune response is a humoral antibody response.

4. The method according to claim 1, wherein said 1918 H1N1 influenza A virus is strain A/Brevig Mission/1/1918 H1N1 influenza A virus.

5. The method according to claim 1, wherein one or more of the nucleic acid sequences comprises a promoter and a polyadenylation signal sequence.

6. The method according to claim 1, wherein one or more of the nucleic acid sequences is contained in an expression plasmid.

7. The method according to claim 1, wherein the method further comprises delivering to the subject an isolated naked nucleic acid sequence encoding neuraminidase (NA) from a pandemic influenza virus.

8. The method according to claim 1, wherein the codons of one or more of the nucleic acid sequences are humanized using codons of highly expressed human proteins.

9. The method according to claim 1, further comprising delivering an adjuvant to the subject.

10. The method according to claim 1, wherein the one or more nucleic acid sequences is administered by saline injection or by gene gun.

11. The method according to claim 10, wherein the one or more nucleic acid sequences is coupled to particles.

12. The method according to claim 6, wherein the nucleic acid sequence encoding M or the nucleic acid sequence encoding NP, and the nucleic acid sequence encoding HA, are contained in a single expression plasmid.

13. The method according to claim 12, wherein the naked nucleic acid sequence encoding M and the naked nucleic acid sequence encoding NP and the naked nucleic acid sequence encoding HA are contained in a single expression plasmid.

14. The method according to claim 7, wherein said NA and HA are from the same pandemic influenza virus.

* * * * *